United States Patent
Russell et al.

(10) Patent No.: US 10,954,506 B2
(45) Date of Patent: *Mar. 23, 2021

(54) POLYMER ENGINEERED REGENERATING BIOSCAVENGERS

(71) Applicant: Carnegie Mellon University, Pittsburgh, PA (US)

(72) Inventors: Alan J. Russell, Gibsonia, PA (US); Hironobu Murata, Pittsburgh, PA (US); Chad S. Cummings, Pittsburgh, PA (US); Richard R. Koepsel, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,739

(22) Filed: Aug. 30, 2019

(65) Prior Publication Data

US 2019/0382749 A1    Dec. 19, 2019

Related U.S. Application Data

(62) Division of application No. 15/026,093, filed as application No. PCT/US2014/059171 on Oct. 3, 2014, now Pat. No. 10,400,232.

(60) Provisional application No. 61/961,097, filed on Oct. 3, 2013.

(51) Int. Cl.

| | |
|---|---|
| *C12N 9/96* | (2006.01) |
| *A61K 38/46* | (2006.01) |
| *C12N 9/16* | (2006.01) |
| *A61K 47/58* | (2017.01) |
| *C12N 11/08* | (2020.01) |
| *A61K 38/48* | (2006.01) |
| *C12N 9/76* | (2006.01) |

(52) U.S. Cl.
CPC .............. *C12N 9/96* (2013.01); *A61K 38/465* (2013.01); *A61K 38/4826* (2013.01); *A61K 47/58* (2017.08); *C12N 9/16* (2013.01); *C12N 9/6427* (2013.01); *C12N 11/08* (2013.01); *C12Y 301/01007* (2013.01); *C12Y 304/21001* (2013.01)

(58) Field of Classification Search
CPC ......... C12N 11/00; C12N 11/02; C12N 11/08; C12N 11/06; C12N 9/16; C12N 9/96; C12Y 301/01007; C12Y 301/21001; A61K 47/58; A61K 38/465; A61K 38/4826

See application file for complete search history.

(56) References Cited

U.S. PATENT DOCUMENTS

| | | |
|---|---|---|
| 4,350,801 A | 9/1982 | Grasshoff |
| 6,291,200 B1 | 9/2001 | LeJeune et al. |
| 6,642,037 B2 | 11/2003 | Gordon et al. |
| 6,759,220 B1 | 7/2004 | LeJeune et al. |
| 7,572,764 B2 | 8/2009 | Cohen et al. |
| 7,722,838 B2 | 5/2010 | Hyacinthe |
| 2008/0206182 A1 | 8/2008 | Sommermeyer et al. |
| 2011/0091957 A1 | 4/2011 | Lele et al. |
| 2013/0058910 A1 | 3/2013 | Koepsel et al. |
| 2013/0071394 A1 | 3/2013 | Trover et al. |

FOREIGN PATENT DOCUMENTS

| | | | |
|---|---|---|---|
| WO | WO 02/083708 | 10/2002 | |
| WO | WO-2016061562 A2 * | 4/2016 | ............... C12N 9/96 |

OTHER PUBLICATIONS

Gordon et al. "Organophosphate skin decontamination using immobilized enzymes" Chemico-Biological Interactions 119-120 (1999) 463-470 (Year: 1999).*
Amitai et al., "Decontamination of chemical and biological warfare agents with a single multi-functional material," Biomaterials, 2010, 31(15):4417-4425.
Ashani et al., "Estimation of the upper limit of human butyrylcholinesterase dose required for protection against organophosphates toxicity: A mathematically based toxicokinetic model," Toxicological Sciences, 2004, 77(2):358-367.
Averick et al., "ATRP under biologically relevant conditions: Grafting from a protein." ACS Macro Letters, 2012, 1(1):6-10.
Baldassane et al., "Detection of endoplasmic reticulum stress markers and production enhancement treatments in transgenic goats expressing recombinant human butyrylcholinesterase," Transgenic Res., 2011, 20(6):1265-1272.
Benschop et al., "Nerve agent stereoisomers: analysis, isolation and toxicology," Acc. Chem. Res., 1988, 21:368-374.
Bigley et al., "Enzymatic neutralization of the chemical warfare agent VX: Evolution of phosphodiesterase for phosphorothiolate hydrolysis," J. Am. Chem. Soc.., 2013. 135(28):10426-10432.
Cummings et al., "Tailoring enzyme activity and stability using polymer-based protein Engineering," Biomaterials, 2013. 34:7437-7443.
Drevon et al., "Enzyme-containing Michael-adduct-based coatings," Biomacromolecules, 2003, 4(3):675-682.
Eddleston et al., "Management of acute organophosphorus pesticide poisoning," Lancet, 2008, 371:597-607.
Estevez et al., "Model equations for the kinetics of covalent irreversible enzyme inhibition and spontaneous reactivation: Esterases and organophosphorus compounds," Crit. Rev. Toxicol., 2009, 39(5):427-448.
Evyer, Peter, "The role of oximes in the management of organophosphorus pesticide poisoning," Toxicol. Rev., 2003, 22(3):165-190.
Gauthier et al., "Polymer-protein conjugates: An enzymatic activityperspective," Polym. Chem., 2010, 1(9);1341-1520.
Goldsmith et al., "Enzyme engineering by targeted libraries," Meth. Enzymol., 2013, 523:257-283.

(Continued)

*Primary Examiner* — Thane Underdahl

(74) *Attorney, Agent, or Firm* — Fish & Richardson P.C.

(57) ABSTRACT

Embodiments of the invention provide at least one polymer covalently conjugated to an esterase. The at least one polymer includes a plurality of oxime functional groups.

4 Claims, 20 Drawing Sheets

(56) References Cited

OTHER PUBLICATIONS

Figure 1:
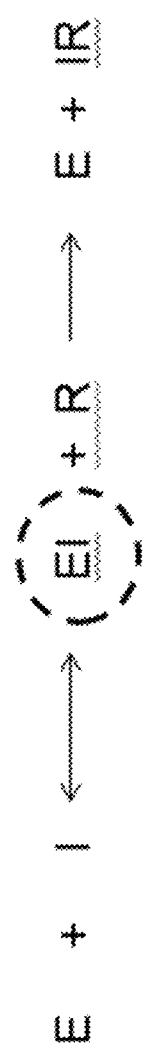

Gulla et al. "Reactivation of immobilized acetyl cholinesterase in an amperometric biosensor for organophosphorus pesticide," Biochim. Biophys. Acta, 2002, 1597:133-139.

Gupta et al.. "Directed evolution of hydrolases for prevention of G-type nerve agent intoxication," Nature Chemical Biology, 2011. 7(2):120-125.

Kitz et al., "Activity-structure relationships in the reactivation of diethyiphosphoryl acetylcholinesterase by phenyl-1-methyl pyridinium," Biochem. Pharmacol., 1965, 14(10):1471-1477.

Kolb et al., "Click chemistry: Diverse chemical function from a few good reactions," Angew. Chem. Int. Ed., 2001, 40(11):2004-2021.

Konkolewicz et al., "ICAR ATRP with ppm Cu catalyst in water," Macromolecules, 2012, 45(11):4461-4468.

Kovarik et al., "Mutation of acetylcholinesterase to enhance oxime-assisted catalytic turnover of methylphosphonates," Toxicol., 2007, 233:79-84.

Kovarik et al., "Oximes: Reactivators of phosphorylated acetylcholinesterase and antidotes in therapy against tabun poisoning." Chemical-Biological Interactions, 2008, 175(1-3):173-179.
Kuca et al., "Synthesis of the three monopyridinium oximes and evaluation of their potency to reactivate acetylcholinesterase inhibited by nerve agents," J. Appl. Biomed., 2004, 2:51-56.
LeJeune et al., "Covalent linkage of mammalian cholinesterases within polyurethane foams," Proc. Med. Def. Biosc. Rev., 1996. 1:223-230.
Lele et al., "Enhancing enzyme stability, against TiO2-UV induced inactivation," Biomacromolecules, 2005, 6(1):475-482.
Lele et al., "Rational protein modification leading to resistance of enzymes to TiO2-UV irradiation-induced inactivation," Biomacromolecules, 2004, 5(5):1947-1955.
Lele et al., "Synthesis of Uniform Protein-Polymer Conjugates," Biomacromolecules, 2005, 6(6):3380-3387.
Loke et al., "O-Substituted derivatives of pralidoxime: muscarinic properties and protection against soman effects in rats," Eur. J. Pharmacol., 2002, 442:279-287.
Lundy et al., "Development of the bisquaternary oxime HI-6 toward clinical use in the treatment of organophosphate nerve agent poisoning," Toxicological Reviews, 2006. 25(4):211-243.
Masson et al., "Catalytic bioscavengers against toxic esters an alternative approach for prophylaxis and treatments of poisonings," Acta Nature, 2009, 1:68-79.
Matyjaszewski, "Atom transfer radical polymerization (ATRP): Current status and future perspectives," Macromolecules, 2012, 45(10):4015-4039.
Matyjaszewski, "Atom transfer radical polymerization: from mechanisms to applications," Isr. J. Chem., 2012. 52(3-4):206-220.
Mazor et al., "Aging-resistant organophosphate bioscavenger based on polyethylene glycol-conjugated F338A human acetylcholinesterase," Mol. Pharmacol, 2008, 74(3):755-763.
Millard et al., "Design and expression of organophosphorus acid anhydride hydrolase activity in human butyrylcholinesterase." Biochem., 1995; 34(49):15925-15933.
Millard et al., "Organophosphorus acid anhydride hydrolase activity in human butyrylcholinesterase: Synergy results in a somanase," Biochem., 1998, 37:237-247.
Murata et al., "Polymer-based protein engineering can rationally tune enzyme activity, pH-dependence, and stability," Biomacromolecules, 2013, 14(6):1919-1926.
Ordentlich et al., "The role of AChE active site gorge in determining stereoselectivity of charged and noncharged VX enantiomers," Chemical-Biological Interactions, 2005, 157-158:191-198.
Radie, et al., "Catalytic detoxification of nerve agent and pesticide organophosphates by butyrylcholinesterase assisted with non-pyridinium oximes," Biochem. J., 2013. 450:231-242.
Simakova et al., "Aqueous ARGET ATRP," Macromolecules, 2012, 45(16):6371-6379.
Taylor et al., "Acetylcholinesterase: Converting a vulnerable target to a template for antidotes and detection of inhibitor exposure," Toxicology, 2007, 233(1-3):70-78.
Taylor, "Chapter 6, Anticholinesterase Agents," Goodman and Gillman's The Pharmacological Basis of Therapeutics, 7th Ed., Macmillan Publishing Company, New York, 1985, pp. 110-129.
Terrier et al., "Revisiting the reactivity of oximate a-nucleophiles with electrophilic phosphorus centers. Relevance to detoxification of sarin, soman and IDP under mild conditions," Org. Biomol. Chem., 2006, 4(23):4352-4363.
Van Hooidonk et al., "On the reactivity of organophosphorus compounds Part IV. The alkaline hydrolysis of some O-phosphylated 2-pyridine oximes," Rec. Trav. Chim., 1968, 87(7):673-686.

* cited by examiner

POLYMER ENGINEERED REGENERATING BIOSCAVENGERS

CROSS-REFERENCE TO RELATED APPLICATIONS

This application is a divisional of U.S. Ser. No. 15/026,093, filed Mar. 30, 2016, which is a National Stage application under 35 U.S.C. § 371 of International Application No. PCT/US14/59171 having an International Filing Date of Oct. 3, 2014, which claims the benefit of priority from U.S. Provisional Application Ser. No. 61/961,097, filed Oct. 3, 2013. The disclosures of the prior applications are considered part of (and are incorporated by reference in) the disclosure of this application.

FIELD OF THE INVENTION

This invention describes the development of a broad spectrum biocatalytic scavenger for use as an organophosphate (OP) detoxifying agent.

BACKGROUND OF THE INVENTION

The dramatic tragedy in the reemergence of chemical weapons use in Syria highlights like never before the urgent need to provide effective medical countermeasures for nerve agent poisoning. Less talked of, but even more urgent, is the need for countermeasures against organophosphate (OP) pesticide poisoning that kills hundreds of thousands worldwide every year. Although most OP pesticides were banned for use in the US, they still exist and are produced in Kilo-tons in other countries and are easily accessible. Some of them are highly toxic as witnessed by the fatal poisoning of school children in India in July 2013 caused by monocrotophos contamination of cooking oil. OP pesticides are a major worldwide health problem, even without accidental or deliberate release with OP self-poisoning (suicide), responsible for 200,000 deaths a year worldwide. Eddleston M, Buckley N A, Eyer P, Dawson A H. Management of acute organophosphorus pesticide poisoning. *Lancet,* 371: 597-607 (2008). Further, these poisonings are difficult to treat with the current standards of therapy.

SUMMARY OF THE INVENTION

The present investigation represents a solution for the need for countermeasures against organophosphate pesticide poisoning. A broad spectrum regenerating scavenger for use as an OP compound detoxifying agent following acute exposure is described herein.

Accordingly, the present disclosure may include various aspects of a composition and methods for making and using the composition. For example, in various aspects, the invention described herein provides a composition comprising at least one polymer covalently conjugated to an esterase. The at least one polymer may comprise a plurality of oxime functional groups.

In various aspects, the invention may include a composition wherein the esterase may comprise a member selected from the group consisting of acetylcholinesterase and butyrylcholinesterase. In various aspects, the invention may include a composition wherein the esterase may not comprise acetylcholinesterase. In various aspects, the invention may include a composition as provided in any of the aspects described herein, wherein the esterase may not include butyrylcholinesterase.

In various aspects, the invention may include a composition as provided in any of the aspects of the composition described herein, wherein the plurality of oxime functional groups may comprise alkyne derivatives of 2-pyridine aldoxime.

In various aspects, the invention may include a composition as provided in any of the aspects of the composition described herein, wherein the plurality of oxime functional groups may comprise an aldoxime. In various aspects, the invention may include a composition as provided in any of the aspects of the composition described herein, wherein the plurality of oxime functional groups may comprise a ketoxime. In various aspects, the invention may include a composition as provided in any of the aspects of the composition described herein, wherein the plurality of oxime functional groups may comprise at least one bis-pyridinium oxime.

In various aspects, the invention may include a composition as provided in any of the aspects of the composition described herein, wherein the at least one polymer covalently conjugated to the esterase may comprise a long lived covalent conjugate.

In various aspects, the invention may include a composition as provided in any of the aspects of the composition described herein, wherein the long lived covalent conjugate may comprise a conjugate that is maintained in the body for a time period ranging from at least one 24 hour day and preferably for more than about one day to more than about one week. The long lived covalent conjugate may be maintained in the body for a period of time of at least one week, or at least two weeks, and preferably for a period of time sufficient to eliminate or significantly reduce the inhibiting function of the OP toxin.

In various aspects, of the invention, any of the aspects of the composition described herein may comprise at least one polymer which may have at least one environmentally responsive monomer.

In various aspects of the invention, any of the aspects of the composition described herein may comprise, at least one polymer having a polymer length of two repeat units, and preferably greater than two repeat units, and more preferably a polymer length ranging from a minimum of at least 2 monomer repeats to about 1000 monomer repeats. In certain aspects of the composition, there may be greater than 1000 monomer repeats. The only upper limit on the number or length of monomers is that number or length that will avoid hindering contact of the oxime functional group or groups sufficient to interact with the active site of the enzyme for neutralization of the inhibiting moiety.

In various aspects, the invention may include a composition as provided in any of the aspects of the composition described herein, wherein the at least one polymer may be a co-polymer that may comprise at least two different monomers, wherein at least one monomer may comprise a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and combinations thereof.

In various aspects, the invention may include a composition as provided in any of the aspects of the composition described herein, wherein there are a plurality of polymers each covalently conjugated to the esterase, and each polymer may comprise a plurality of monomer units wherein at least one said monomer unit comprises an oxime functional group.

In various aspects, the invention may include a composition as provided in any of the aspects of the composition described herein, wherein a plurality of monomer units of each polymer comprises an oxime functional group.

In various aspects, the invention may include a composition as provided in any of the aspects of the composition described herein, wherein the plurality of polymers comprises co-polymers, each co-polymer comprising at least two different monomers. At least one such monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and combinations thereof.

In various aspects, the invention may include a composition as provided in any of the aspects of the composition described herein, wherein the plurality of polymers comprises a plurality of co-polymers and a plurality of homopolymers. Each co-polymer of the plurality of co-polymers may comprise at least two different monomers, wherein at least one monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and combinations thereof. Each homopolymer of the plurality of homopolymers may comprise a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and combinations thereof.

In certain aspects, the invention may include a composition comprising a bioconjugate which comprises an esterase and at least one polymer covalently conjugated to the esterase. In various aspects, of the bioconjugate, the at least one polymer comprises a plurality of oxime functional groups; and at least one oxime functional group of the plurality of oxime functional groups is positioned to react, in use, with a phosphoryl functional group when an inhibitor having a phosphoryl functional group attaches to an active site of the esterase.

In certain aspects, the invention may include a composition according to any of the aspects of the composition described herein wherein the at least one oxime functional group is positioned to exert a nucleophilic attack on a phosphoryl functional group when, in use, an inhibitor having a phosphoryl functional group attaches to an active site of the esterase, said nucleophilic attack resulting in the removal of the phosphoryl functional group from the active site.

In certain aspects, the invention may include a composition according to any of the aspects of the composition or bioconjugate described herein, wherein the at least one polymer of the bioconjugate may comprise a flexibility sufficient to react, in use, with a phosphoryl functional group when an inhibitor having a phosphoryl functional group attaches to the active site of the esterase.

In certain aspects, the bioconjugate may include any of the aspects of the composition described herein, such as, for example, wherein the esterase is a member selected from the group consisting of acetylcholinesterase, butyrylcholinesterase, and chymotrypsin.

In certain aspects, the invention may include a bioconjugate comprising any of the aspects of the composition described herein, such as, for example, the at least one oxime functional group, wherein such functional group comprises one or more of alkyne derivatives of 2-pyridine aldoxime, an aldoxime or a ketoxime, or at least one bis-pyridinium oxime. In certain aspects, the invention may include a bioconjugate comprising any of the aspects of the composition described herein, such as, for example, wherein the at least one polymer comprises at least one environmentally responsive monomer, and the at least one polymer may comprise a co-polymer comprising at least two different monomers, wherein at least one monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and combinations thereof.

In various aspects, the composition according to any of the aspects described herein may function to reduce or eliminate the effectiveness of an inhibitor which may comprise a member selected from the group consisting of VX, Sarin, Soman, DFP, Paraoxon, Parathion, V classes of OP nerve agents, G classes of OP nerve agents, and combinations thereof.

In another aspect, the invention described herein may include a method comprising administering a bioscavenger according to any of the aspects or combination of aspects of the composition or the bioscavenger described herein to an individual suffering from organophosphate toxin exposure. The individual is preferably a mammal and may be a human victim of OP exposure. The bioscavenger used in the method may comprise for example, at least one polymer covalently conjugated to an esterase, the at least one polymer comprising a plurality of oxime functional groups. The method may further comprise following administration and upon exposure of the bioscavenger to the organophosphate toxin, reacting at least one of the plurality of oxime functional groups with at least one covalently inhibited residue of the esterase to detoxify the organophosphate toxin and regenerate the bioscavenger.

In various aspects, upon exposure of the bioscavenger to the organophosphate toxin, the method as described herein may further comprise reacting at least one of the plurality of oxime functional groups with at least one covalently inhibited residue of the esterase to detoxify the organophosphate toxin and regenerate the bioscavenger.

In certain aspects, the plurality of oxime functional groups of the bioscavenger used in any aspect of the method may comprise an oxime functional group positioned to exert a nucleophilic attack on a phosphoryl functional group when an inhibitor having a phosphoryl functional group attaches to an active site of the esterase. The nucleophilic attack results in the removal of the phosphoryl functional group from the active site.

In various aspects, the invention described herein may be in the form of a bioscavenger comprising any aspect or combination of aspects of the composition described herein. For example, the bioscavenger may comprise at least one polymer covalently conjugated to an esterase, the at least one polymer comprising a plurality of oxime functional groups, wherein at least one of the plurality of oxime functional groups is positioned to exert a nucleophilic attack on a phosphoryl functional group when, in use, a phosphoryl functional group is covalently attached to an active site of the esterase effecting removal of the phosphoryl functional group from the active site and regeneration of the bioscavenger. The at least one polymer of the bioconjugate may comprise any one or more of the aspects of the polymers described herein, and may comprise any one or more of the aspects of the oxime functional groups described herein, and as described above the esterase of the bioconjugate may comprise acetylcholinesterase, butyrylcholinesterase, or chymotrypsin. In certain aspects of the bioscavenger, one or two of acetylcholinesterase, butyrylcholinesterase, or chymotrypsin may be absent from the composition of the bioscavenger. The oxime functional group of the bioscavenger is preferably positioned to exert a nucleophilic attack on a phosphoryl functional group when, in use, an inhibitor having a phosphoryl functional group attaches to an active site of the esterase, said nucleophilic attack resulting in the removal of the phosphoryl functional group from the active site, preferably resulting in the removal of the phosphoryl functional group from the active site.

In one aspect, the invention described herein provides a method for biocatalytic scavenging by using polymer-based protein engineering to conjugate oxime containing polymers directly to enzymes providing a tethered pseudo-cofactor. As used herein, a "pseudo-factor" is a synthetic compound that assists an enzyme in completing a catalytic cycle and which may or may not be consumed in the process. Judicious design of the polymer conjugates and the exquisite synthetic control afforded by atom transfer radical polymerization (ATRP) can provide engineered proteins of broad variation. Averick S E, Konkolewicz D, Matyjaszewski K., Aqueous ARGET ATRP, *Macromolecules*, 45(16):6371-9 (2012); Simakova A, Park S, Konkolewicz D, Magenau A I D, Mehl R A, et al., ATRP under Biologically Relevant Conditions: Grafting from a Protein, *ACS Macro Letters*, 1(1):6-10. (2012); Konkolewicz D, Magenau A J D, Averick S E, Simakova A, He H, Matyjaszewski K., ICAR ATRP with ppm Cu Catalyst in Water, *Macromolecules*, 45(11):4461-8 (2012); Magenau A J D, Averick S E, Simakova A, He H, Matyjaszewski K. ICAR ATRP with ppm Cu Catalyst in Water, *Macromolecules*, 45(11):4461-8 (2012); Matyjaszewski K, Atom Transfer Radical Polymerization: From Mechanisms to Applications, Isr *J Chem.*; 52(3-4):206-20 (2012); Matyjaszewski K, Atom Transfer Radical Polymerization (ATRP): Current Status and Future Perspectives, *Macromolecules*, 45(10):4015-39 (2012).

One of the unmet needs in the treatment of organophosphate (OP) intoxication is a broad spectrum non-stoichiometric antidotal scavenger useful in single occurrence or mass casualty scenarios. Toward that end, the present invention addresses these issues and describes the development of a broad spectrum regenerating scavenger for use as an OP compound detoxifying agent following acute exposure.

The role of acetylcholinesterase (AChE) in nerve and muscle is to terminate the neurotransmission signal exerted by acetylcholine by rapid hydrolysis at a sub-millisecond time scale. The irreversible inhibition of AChE by OP nerve agents and pesticides leads to persistent severe toxic symptoms and death caused by excess acetylcholine in cholinergic synapses in the peripheral and central nervous system. The ability of many OP compounds (e.g., VX, Sarin, Soman, DFP, Paraoxon, G-agents, V-agents, Parathion, and the like) to irreversibly inhibit AChE catalytic activity is due to the hydrolysis of the OP compound within the active site of the enzyme with the concomitant formation of a covalent bond between the phosphoryl moiety of the OP and the catalytic serine residue within the enzyme active site. The inhibition of the various members of the cholinesterase family by OP compounds is dependent upon how the three dimensional structure of a given OP fits within the three dimensional structure of the enzyme active site. All of the cholinesterases are venerable to inhibition by one or more OP compound. Covalent modification by organophosphate inhibition prevents AChE from completing a catalytic cycle thus locking it in an intermediate catalytically inactive state. Enzymes within the serine protease family (e.g., chymotrypsin and trypsin) have active site architectures that are similar to the cholinesterases and similarly inhibited by some organophosphate compounds. Green A L and Nicholls J., The Reactivation of Phosphorylated Chymotrypsin, *Biochem J.*, 72(1): 70-75 (1959). Some molecules with oxime functionality, For example, 2-pyridine aldoxime (2-PAM), toxogonin (obidoxime), MMB-4 (methoxime) and HI-6 (asoxime chloride), constitute the very few clinically approved antidotes to OP intoxication. The antidotal oximes function by reacting with the phosphonylated serine in the enzyme active site regenerating enzyme activity. For the purposes of discussion consider an oxime reaction with an OP-inhibited enzyme to be the final step in the catalytic hydrolysis of OP toxins (pesticides and nerve agents) in that it releases a non-toxic alkyl-phosphonate as a product of the reaction and returns the enzyme to its active state.

Current antidote therapies couple oxime drugs with atropine (a muscarinic cholinergic antagonist) and anticonvulsants. While the quaternary oximes are generally considered effective in the short term, the rapid clearance of oximes such as 2-PAM from circulation in the body combined with the long residence times and relatively slow adsorption and distribution rates of OP nerve agents and pesticides especially following dermal (OP pesticides and VX) or buccal exposure (pesticides) reduces their effectiveness in cases of single occurrence or mass contamination and intoxication events where individualized continuous care is not practical.

It should be noted that the current generation of therapeutic oximes are stoichiometric chemical scavengers as they are consumed in their reaction with the OP. The kinetics of oxime-induced reactivation and rapid AChE inhibition by OP compounds are not compatible with long intervals between oxime dosing. While oxime onset time is relatively fast, the retention time in blood is short after a single intra-muscular oxime injection as the elimination from blood to urine of 2-PAM has at $\frac{1}{2}$ of just 60 minutes. On the other hand, the time of peak ChE inhibition caused by nerve agents in the peripheral nervous system and the central nervous system occurs at around 1 hour, where 50% of the oxime is already gone. Thus, there is a need for detoxifying agents that can cover the time span of the immediate emergency treatment with continuous detoxifying treatment without the logistic burden of applying repeated injections of oximes.

In order to meet the need for detoxifying agents that can cover the time span of both immediate and continuous treatment, the compositions of the present invention, in at least one or more aspects, comprise esterase, such as cholinesterases (ChEs), covalently conjugated with polymer brushes composed of tethered oxime side chains, thereby converting them into a wide spectrum of regenerating OP-degrading enzymes. The tethered oxime polymers act as pseudo-prosthetic groups allowing a complete catalytic cycle of the OP substrate by reactivating the OP-inhibited enzyme.

Additionally, because oximes can also react directly with free OP compounds in solution, the enzyme-polyoxime conjugates can increase the lifetime of the scavenger activity and act as active nucleophiles that directly attack OP molecules resulting in their detoxification. Thus, the enzyme polyoxime conjugate also functions as a long lived oxime delivery system in that the enzyme can delay clearance of the oxime antitoxin from the body. For example, an esterase polymer conjugate can result in the long lived presence of the oxime over a period ranging from at least about one day to about a week, and preferably more than one week.

It should be understood that this disclosure is not limited to the various aspects or embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures.

FIG. 1 is a schematic illustration of a conventional stoichiometric bioscavenger showing the stoichiometric binding and sequestering of an inhibitor (I) by formation of an enzyme (E)/inhibitor complex (EI). Additionally shown in FIG. 1 is the regeneration of the enzyme (E) with regenerating molecule (R) to form an inhibitor/regenerating molecule complex (IR).

FIG. 2 is a schematic illustration of a regenerating bioscavenger enzyme (ER4) that cleaves an organophosphate toxin substrate (I) into non-toxic molecules (Io).

FIGS. 3A-3F are schematic diagrams and characterization data verifying the synthesis of an acetylcholinesterase poly-2-PAM covalent conjugate. FIG. 3A is a schematic diagram of the synthesis of a bromine containing polymer. FIG. 3B is an $^1$H NMR spectrum verifying the structure of the bromine containing polymer of FIG. 3A.

FIG. 3C is a schematic of the quaternization of the polymer of FIGS. 3A and 3B with 2-PAM. FIG. 3D is an $^1$H NMR spectrum verifying the structure of the 2-PAM containing polymer product of FIG. 3C. FIG. 3E is a schematic of the generation of an NHS group on the 2-PAM containing polymer of FIGS. 3C and 3D. FIG. 3F is a schematic of the conjugation of the 2-PAM containing polymer of FIG. 3E with AChE.

FIGS. 4A and 4B are schematic diagrams and characterization data verifying the synthesis of an acetylcholinesterase-sulfonate polymer conjugate. FIG. 4A is a schematic diagram illustrating acetylcholinesterase polysulfonate covalent conjugate formation by "grafting from" or "surface initiated" atom transfer radical polymerization (ATRP). FIG. 4B is an $^1$H NMR spectrum verifying the structure of the acetylcholinesterase-sulfonate polymer conjugate of FIG. 4A.

FIG. 5 is data of an enzyme activity assay indicating the percent acetylcholinesterase activity recovered (post inhibition with paraoxon) over time showing self-reactivation of the inhibited acetylcholinesterase poly-2-PAM covalent conjugate of FIG. 3F as compared to the native acetylcholinesterase.

FIGS. 6A-6E are schematic diagrams and characterization data verifying the synthesis of an acetylcholinesterase poly-DMAA-2-PAM covalent conjugate synthesized using ATRP. FIG. 6A is a schematic of "surface initiated" ATRP of DMAA and an azide monomer from an AChE-initiator conjugate. FIG. 6B is an $^1$H NMR spectrum verifying the structure of the AChE-PDMAA/Azide conjugate of FIGS. 6A and 6B. FIG. 6C is a schematic of the "Click" chemistry addition of an alkyne-2-PAM reagent to the AChE-PDMAA/Azide conjugate of FIG. 6C. FIG. 6D is an $^1$H NMR spectrum verifying the structure of the AChE-PDMAA/2-PAM conjugate of FIG. 6C. FIG. 6E is an $^1$H NMR spectrum verifying the structure of the alykyne-2-PAM reagent used in FIG. 6C in the synthesis of the AChE-PDMAA/2-PAM conjugate.

FIGS. 7A and 7B are schematic diagrams contrasting the predicted reactivation pathways for enzyme polymer attached aldoximes and ketoximes.

FIG. 8 is data showing enzyme activity of AChE-polymer conjugates. The enzyme activity was shown to be dependent on the chemistry of the attached polymer.

FIG. 9 is data showing enzyme activity of a chymotrypsin-polymer conjugate.

DETAILED DESCRIPTION OF THE INVENTION

The present invention provides a regenerating bioscavenger for detoxification against organophosphate (OP) poisoning.

Various embodiments or aspects of the invention are described and illustrated in this specification to provide an overall understanding of the structure, function, operation, manufacture, and use of the disclosed compositions, systems, and methods. It is understood that the various embodiments or aspects described and illustrated in this specification are non-limiting and non-exhaustive. Thus, the invention is not limited by the description of the various non-limiting and non-exhaustive aspects or embodiments disclosed in this specification. Rather, the invention is defined solely by the claims. The features and characteristics illustrated and/or described in connection with various aspects or embodiments may be combined with the features and characteristics of other aspects or embodiments. Such modifications and variations are intended to be included within the scope of this specification. As such, the claims may be amended to recite any features or characteristics expressly or inherently described in, or otherwise expressly or inherently supported by, this specification. The various aspects or embodiments disclosed and described in this specification can comprise, consist of, or consist essentially of, or be characterized by the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference herein.

Reference throughout this specification to "various aspects" or "various embodiments," or the like, means that a particular feature or characteristic may be included in an aspect or embodiment. Thus, use of the phrase "in various aspects or embodiments," or the like, in this specification does not necessarily refer to a common aspect or embodiment, and may refer to different aspects and/or embodiments. Further, the particular features or characteristics may be combined in any suitable manner in one or more aspects or embodiments. Thus, the particular features or characteristics illustrated or described in connection with various aspects or embodiments may be combined, in whole or in part, with the features or characteristics of one or more other aspects or embodiments without limitation. Such modifications and variations are intended to be included within the scope of the present specification.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all subranges of the same numerical precision subsumed within the recited range. For example, a range of 1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such sub-ranges would comply with the applicable disclosure requirements.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

"Bound," "bind", "binding", "associated with", or "attachment", "attached to" and the like as used herein with respect to the composition, and substituents, groups, moieties, and the like of the composition or the OP as described herein means, unless otherwise stated, covalent or non-covalent binding, including without limitation, the attractive intermolecular forces between two or more compounds, substituents, molecules, ions or atoms that may or may not involve sharing or donating electrons. Non-covalent interactions may include ionic bonds, hydrophobic interactions, hydrogen bonds, van der Waals forces (dispersion attractions, dipole-dipole and dipole-induced dipole interactions), intercalation, entropic forces, and chemical polarity.

As used herein, the term "non-toxic" refers to materials that are chemically and/or "biologically inert" or inactive with respect to biological organisms.

As used herein the term "polymer length" refers to the length of the polymer as a result of the number of monomers incorporated therein. A "monomer" is a molecule that may bind chemically to other molecules to form a polymer.

As used herein the term "active oxime identity" refers to the identity of an oxime functional group that is capable of interacting with molecules within the active site of an enzyme.

As used herein the term "catalyst" refers to a substance that can cause a change in the rate of a chemical reaction without itself being consumed in the reaction; the changing of the reaction rate by use of a catalyst is called catalysis.

As used herein the term "enzyme" refers to any of a group of catalytic proteins that are produced by living cells and that mediate and promote the chemical processes of life without themselves being altered or destroyed. Consonant with their role as biological catalysts, enzymes show considerable selectivity for the molecules upon which they act (called substrates). As used herein, the terms "active site" and "enzyme active site" refers to a specific region of an enzyme where a substrate binds and catalysis takes place (binding site).

As used herein the term "inhibitor" refers to a substance that diminishes the rate of a chemical reaction often by binding within the active site in a process is referred to as "inhibition." In enzyme-catalyzed reactions an inhibitor frequently acts by binding to the enzyme, in which case it may be referred to as an "enzyme inhibitor."

As used herein, the term "bioscavenger" refers to molecules and proteins that function to either stoichiometrically bind and sequester the inhibiting molecule(s) or by catalytically or regeneratively cleaving the inhibiting substrate or inhibiting molecules into non-toxic products. The term "stoichiometric bioscavenger(s)" refers to those bioscavenger molecules and proteins that function to stoichiometrically bind and sequester inhibiting molecule(s). Likewise, the term "regenerating bioscavenger(s)" or "regenerative bioscavenger(s)" refers to those bioscavenger molecules and proteins that function by cleaving the inhibiting substrate or inhibiting molecules into a non-toxic product.

As used herein the term "alkyl" refers to a straight-chained or branched hydrocarbon. Examples of alkyl groups include methyl, ethyl, n-propyl, isopropyl, tert-butyl, and n-pentyl. Similarly, the term "alkenyl" or "alkynyl" refers to a straight-chained or branched hydrocarbon containing one or more C=C double bonds or one or more C≡C triple bonds.

As used herein the term "free ChE," "free enzyme," "free esterase," "free AChE," or the like refers to native-type enzymes that are not modified by polymers, radicals, combinations thereof, or the like. As used herein the term "free oxime," or "free oximes" refers to molecules including an oxime functional group that are not conjugated to an enzyme or polymer and are circulating in solution.

As used herein the term "functional group" refers to specific groups of atoms or bonds within molecules that are responsible for the characteristic chemical reactions of those molecules. As used herein the term "phosphoryl functional group" refers to derivatives of phosphoric acid.

As used herein the term "oxime" refers to a chemical compound belonging to the imines, with the general formula R1R2C=NOH, where R1 is an organic side-chain and R2 may be hydrogen, forming an aldoxime, or another organic group, forming a ketoxime. 0-substituted oximes form a closely related family of compounds. Amidoximes are oximes of amides with general structure RC(=NOH)(NRR'). Oximes are usually generated by the reaction of hydroxylamine and aldehydes or ketones. As used herein the term "pseudo-catalytic" refers to enzyme conjugated oximes that generate a further oxime upon hydrolysis.

As used herein the term "esterase" refers to a hydrolase enzyme that splits esters into an acid and an alcohol in a chemical reaction with water called hydrolysis. Cholinesterase is a family of esterases including acetylcholinesterase and butyrylcholinesterase. Acetylcholinesterase (AChE) is an enzyme that degrades (through its hydrolytic activity) the neurotransmitter acetylcholine, producing choline and an acetate group. Butyrylcholinesterase (BChE or BuChE) is a non-specific cholinesterase enzyme that hydrolyses many different choline esters.

As used herein an "enzyme polyoxime conjugate," and "enzyme polymer conjugate" refers to an enzyme or esterase that has been modified to include a polymer or polyoxime into its protein structure. The esterase polymer conjugate described can be in the free form or in the form of salt, if applicable. A salt, for example, can be formed between an anion and a positively charged group (e.g., amino) on a protein-polymer conjugate of this invention. Suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a protein-polymer conjugate of this invention. Suitable cations include sodium ion, potassium ion, magnesium ion, calcium ion, and an ammonium cation such as tetramethylammonium ion. In addition, the esterase polymer conjugate may have one or more double bonds, or one or more asymmetric centers. Such a conjugate can occur as racemates, racemic mixtures, single enantiomers, individual diastereomers, diastereomeric mixtures, and cis- or trans- or E- or Z-double bond isomeric forms.

As used herein, the term "long-lived" refers to a period of time that is greater than about one day. As used herein the term "maintained in the body" refers to the maintenance of the integrity of the chemical structure of the covalent conjugate without suffering biological or chemical degradation.

As used herein, the term "environmentally responsive" monomer refers to a monomer comprising molecules that react to a change in an environmental stimulus such as a change in pH, a change in light energy, a change in the electrical charge, a change in temperature, a change in pressure, or the like.

As used herein, the term "flexibility" refers to a physical ability of a polymer, monomer, co-polymer, or the like, to bend without incurring structural damage.

As used herein, the term "bioconjugate" refers to the product of the formation of a covalent link between two biomolecules or between a biomolecule and a non-biomolecule. The term "biomolecules" or "biomolecule" refers to any molecule produced by a living organism.

One conventional investigational approach has been the use of stoichiometric bioscavengers to remove OP toxins from circulation. FIG. 1 is a schematic illustration of a stoichiometric bioscavenger showing the stoichiometric binding and sequestering of an inhibitor by formation of an enzyme and inhibitor complex. As shown in FIG. 1, the formation of a typical overall enzyme-inhibitor complex is illustrated as an enzyme E reacting with an inhibitor I, to form the enzyme-inhibitor complex EI (as shown in FIG. 1 within a dashed circle). The double headed arrow of FIG. 1 indicates that the reaction of the enzyme E and the inhibitor I to form the enzyme-inhibitor complex EI occurs stoichiometrically in both directions. Regeneration of the enzyme-inhibitor complex EI may occur by reacting the enzyme-inhibitor complex EI with a free regenerating molecule R. As shown in FIG. 1, the regenerating molecule R bonds to the inhibitor I of the enzyme-inhibitor complex EI removing the inhibitor I from the complex EI to form end products of a regenerated enzyme E and a non-toxic inhibitor-regenerating molecule compound IR. The enzyme kinetics of the regeneration of the enzyme E is controlled by the stoichiometric amounts of free regenerating molecule R and enzyme-inhibitor complex EI present. Enzymes from many sources with a variety of activities against OP compounds have been investigated as potential regenerating bioscavengers. The development of mutated OP hydrolyzing enzymes as regenerating bioscavengers of nerve agents and pesticides, cloned either from bacterial sources (phosphotriesterases, PTEs) or non-human mammalian origin (serum paraoxonase 1, PON1), have demonstrated significant progress in terms of their catalytic efficacy (kcat/Km) in hydrolyzing nerve agents. However, the versatility toward different OP compounds (i.e. G- and V-agents) and immune-compatibility has to be further examined. While many of these OP hydrolases show promise for decontamination of OP compounds, if OP compounds are considered to be pseudo-substrates of AChE, then none of the proposed enzymes has the substrate range of AChE. Pertinently, cholinesterases are inhibited by all toxic OP pesticides and nerve agents and the only differences between the various OP inhibitors are their kinetics of AChE and BChE inhibition.

Thus, the present investigation considers converting cholinesterases from stoichiometric to regenerating bioscavengers to gain efficient detoxification towards numerous OP compounds, both known and unknown (such as, G-agents, a family of agents named for their German inventors, and V nerve agents, a second family of agents believed to be named for viscosity, venomous, or victory as well as thio-OP and oxo-OP pesticides). In contrast, the development of OP hydrolase (OPH) (e.g., OPH and PONI) usually requires tailoring the enzyme mutants toward specific P—X bonds of OP compounds (where X is the leaving group, OR, SR or halogen). Moreover, G- and V-nerve agents are chiral compounds containing optical isomers with different stereochemistry of substituents around the phosphorus atom. The Sp stereoisomer of G-agents such as sarin and cyclosarin and V-agents such as O-ethyl S-[2-(diisopropylamino)ethyl] methylphosphonothioate (VX) is more toxic than its Rp counterpart by 2-3 orders of magnitude. The naturally occurring PTE and PONI detoxify the less toxic Rp isomer more rapidly and tremendous efforts have been made to convert the stereospecificity of PTE and PONI by genetic manipulations. Conversely, AChE and BChE are inhibited more rapidly by the Sp isomer of nerve agents. For instance, AChE is inhibited by Sp-VX 115-fold more rapidly than by Rp-VX, and therefore both AChE and BChE could serve as native protein scavengers for rapid detoxification of these toxic OP stereoisomers.

With the current tool set, a universal antitoxin would require a mixture of enzymes to cover all contingencies. This consideration has led to mutational studies of native ChEs to develop enzymes capable of degrading a wide variety of OP compounds. These studies have produced engineered enzymes that have some catalytic activity toward multiple OP compounds but their catalytic activities were limited. Millard C B, Lockridge 0, Broomfield C A., Organophosphorus acid anhydride hydrolase activity in human butyrylcholinesterase: synergy results in a somanase, *Biochemistry*, 37(1):237-47 (1998); Millard C B, Lockridge 0, Broomfield C A., Design and expression of organophosphorus acid anhydride hydrolase activity in human butyrylcholinesterase, *Biochemistry*, 34(49):15925-33 (1995).

Much of the work regarding stoichiometric bioscavengers has centered on the use of human butyrylcholinesterase (HuBChE), an adventitious natural bioscavenger found as soluble protein in human plasma. Bioscavengers are designed to lower the concentration of the toxin in the blood thus keeping the OP compounds from reaching their AChE targets in the peripheral nervous system and the central nervous system. The key to using bioscavengers like butyrylcholinesterase (BChE) is to maintain high serum concentrations and binding potential at effective levels. Native BChE concentration in plasma is about 50-80 nM, well below that needed to neutralize a lethal dose of OP. An effective dose of BChE against exposure to OP at several times the LD50 (defined as lethal dose that kills half of the test animals under controlled conditions), would be about 3 mg/kg iv (or 210 mg per 70 kg body weight). Processing all of the expired human plasma in U.S. blood banks or Red Cross stocks for an entire year would result in only about 5,000 such HuBChE doses. Cloned sources of HuBChE have been developed to increase production of the enzyme but the enzyme must be processed post-purification because of sialylation differences in the producing cells adding to the cost. Transgenic goats which produce recombinant HuBChE in their milk have been under development for some time but display problems with lactation that have delayed their use as an alternative source of HuBChE.

Figure 2:
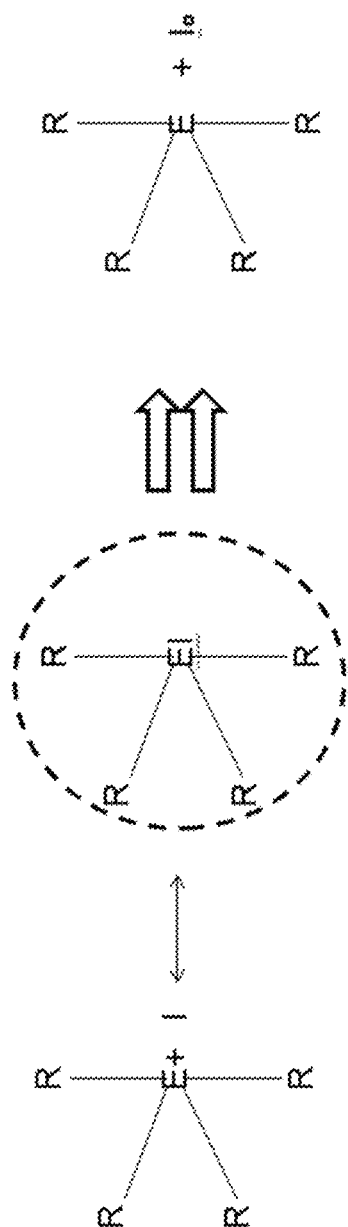

An improved alternative to a stoichiometric bioscavenger is a regenerating bioscavenger. FIG. 2 is a schematic illustration of a novel regenerating bioscavenger enzyme that cleaves the OP toxin substrate into biologically inert molecules, or molecules that are chemically non-harmful to organisms, also known as non-toxic molecules. The bioscavenger of FIG. 2 employs an enzyme E including covalently attached regenerating molecules Rn, where n is more than one or a plurality of regenerating molecules bound to the enzyme. Following reaction with an inhibitor I, the enzyme E and attached regenerating molecules Rn form a complex with the inhibitor I (see FIG. 2 within the dashed-line ellipse). As illustrated, once the enzyme E/regenerating molecules Rn/inhibitor I complex is formed at least one regenerating molecule R reacts with the inhibitor I to form the end products of a biologically inert inhibitor Io compound, and a regenerated bioscavenger enzyme E including the regenerating molecules Rn. The initial hydrolysis of the full OP followed cleavage of the phosphoryl from the active site serine results two non-reactive molecules. Double arrows in FIG. 2 represent the rapid kinetics afforded by the multiple regenerating molecules at the enzyme site which react instantaneously (i.e., at a rate equal to or approximately equal to the rate of diffusion) with the inhibitor or OP molecule inhibiting the active site to regenerate and detoxify the enzyme.

The present investigation considers a hybrid approach of coupling the advantages of first and second generation oximes (which are pseudo-catalytic versus stoichiometric in that they generate a further oxime upon hydrolysis) with native and engineered esterases. Indeed, this approach has resulted in OP compound detoxification in solution together with regeneration of the enzyme polyoxime conjugate described herein. The degree of regenerative cycling is of course limited by the number of oximes available per enzyme molecule but all enzymes suffer in stability during turnover even with natural substrates. However, as mentioned above, the short half-life of oximes in vivo limits the use of free oximes as unbound pseudo-cofactors for cholinesterases.

The present investigation describes a solution to the current state of scavenging by using polymer-based protein engineering to conjugate oxime containing polymers directly to esterases providing a tethered pseudo-cofactor. Precisely engineered design of the polymer conjugates and the advantages of controlled radical polymerization (such as ATRP) can provide the engineered esterase polymer conjugates protection from immune surveillance and extended serum residence times.

Polymer-Based Protein Engineering.

According to various aspects of the present invention, enzymes, and in particular esterases such as the cholinesterases chymotrypsin may be modified and immobilized to target chemical agents. It has been shown that polymer binding to multiple sites on the enzyme surface, as is described herein, does not significantly alter enzyme activity of the esterase. As shown in LeJeune, K. E., Frazier, D. S., Caranto, G. R., Maxwell, D. M., Amitai, G., Russell, A. J. and Doctor, B. P., Covalent linkage of mammalian cholinesterases within polyurethane foams, *Proc. Med Def Biosc. Rev.*, vol. 1, 223-230 (1996), the nerve agent detection system developed with the Agentase/FLIR® is based on multipoint binding to amine groups of AChE to polyurethane foams. See also, U.S. Pat. Nos. 6,759,220 and 6,291,200.

Most of the current techniques for polymer modification of proteins depend upon a "grafting to" approach where pre-formed polymers are conjugated to chemically reactive amino acid side chains. N-hydroxysuccinimide (NHS) chemistry is used to modify the available amine groups primarily at surface available lysine residues. This has been used in many previous enzyme modification studies most notably by modifying chymotrypsin with polymers that contained radical sinks which protected the enzyme activity on TiO2 surfaces under intense UV illumination. These studies showed that polymer conjugation could provide additional functionality to enzymes. A possible drawback of "grafting to" conjugation is that not all available sites may be conjugated leading to a non-homogeneous product that may complicate analysis and give batch dependent results.

In recent work, NHS chemistry was used to bind a specially designed polymerization initiator, N-2-bromo-2- methylpropanoyl-J3-alanine N-hydroxysuccinimide ester to free amine groups on chymotrypsin in aqueous buffer followed by atom transfer radical polymerization (ATRP) which has recently been configured to include reactions that take place in fully aqueous conditions. See PCT/US2014/035033 filed 22 Apr. 2014; Murata H, Cummings C S, Koepsel R R, Russell A J, Polymer-Based Protein Engineering Can Rationally Tune Enzyme Activity, pH-Dependence, and Stability, *Biomacromolecules,* 10:14(6):1919-26 (2013); Cummings C, Murata H, Koepsel R, Russell A J, Tailoring enzyme activity and stability using polymer-based protein engineering, *Biomaterials,* 34: 7437-7443 (2013); Matyjaszewski K., Atom Transfer Radical Polymerization: From Mechanisms to Applications, *Jsr J Chem.* 52(3-4): 206-20 (2012); Matyjaszewski K., Atom Transfer Radical Polymerization (ATRP): Current Status and Future Perspectives, *Macromolecules,* 45(10):4015-39 (2012), each incorporated herein by reference.

Using an initiator and ATRP under aqueous conditions dense poly-N,N-dimethylaminoethyl methacrylate (DMAEMA)-chymotrypsin conjugates were synthesized with relatively narrow molecular weight distributions. The chymotrypsin-PDMAEMA conjugates had higher relative enzyme activities compared to native chymotrypsin below pH 8. Indeed, the conjugates had a ten-fold higher enzyme activity than native enzyme at pH 5. Poly-DMAEMA (PDMAEMA) is a pH-responsive polymer with a condensed conformation above pH 8 and an open extended form at lower pH. With the polymer-enzyme conjugate, points of inflection in the pH-activity profiles were observed that coincided with points at which the molecular conformation of the conjugate changed. In the experiments described in PCT/US2014/035033, Murata H, et al., Biomacromolecules, (2013) (supra); and Cummings C, et al., *Biomaterials,* (2013) (supra), nearly saturated conjugation with 12 of 13 potential sites modified was achieved. These results demonstrate that high density polymer conjugation is achievable and that conjugates using responsive polymers can influence enzyme behavior. The active site residues of the serine protease chymotrypsin are similar to those of the cholinesterases with the mechanistically critical nucleophilic serine residue being the site of inhibition in the cholinesterases.

The present invention advances the understanding of enzymatic mechanisms as well as polymer-oxime and polymer-enzyme interactions especially those involved in mitigating contamination by OP Chemical Warfare Nerve Agents (CWNA). Converting ChE from a stoichiometric bioscavenger (i.e., free ChE and/or free oximes) into a regenerating bioscavenger (i.e., ChE polyoxime conjugate) may reduce significantly (1-2 orders of magnitude) the required protein dose of ChE for injection and thus provide a reasonably inexpensive alternative to stoichiometric bioscavengers and a longer acting antitoxin than free oximes alone.

In various aspects, the present investigation describes the engineering of a polymer-protein conjugate composed of a polymer or polymers containing oxime functionality with an enzyme from the esterase group. Enzymes from the esterase group may include cholinesterase, acetylcholinesterase, butyrylcholinesterase, and chymotrypsin. Alternative names for acetylcholinesterase are known to persons having ordinary skill in the art. For example, alternative names for acetylcholinesterase include RBC cholinesterase, erythrocyte cholinesterase, serum cholinesterase, acetylcholine acetylhydrolase, acetylhydrolase, and forms of acetylcholinesterase encoded by the AChE gene(s), AChE, AChET, AChEH, and AChER. Alternative names for butyrylcholinesterase are also known to persons having ordinary skill in the art. For example, alternative names for butyrylcholinesterase include BChE, BuChE, pseudocholinesterase, plasma cholinesterase, or acylcholine acylhydrolase.

In various aspects, the plurality of oxime functional groups of the esterase polymer conjugate composition comprises an aldoxime. More specifically, the aldoxime may comprise 2-pyridine aldoxime (2-PAM). Also known as Pralidoxime, or 2-pyridine aldoxime methyl chloride usually as the chloride or methiodide salts is a member of the oxime group of compounds that bind to organophosphate-inactivated acetylcholinesterase. The 2-PAM aldoxime monomer has the ability to attach to an unblocked anionic site of the inhibiting acetylcholinesterase enzyme. The 2-PAM subsequently binds to the organophosphate inhibiting molecule. The organophosphate once bound to the 2-PAM oxime molecule changes conformation and is released from its binding to the acetylcholinesterase enzyme active site. The disjoined OP inhibitor/2-PAM oxime antidote then unbinds from the enzyme, which is now able to function again.

In various aspects, the plurality of oxime functional groups may comprise a ketoxime. A ketoxime is similar in structure to an aldoxime as both are of the oxime group of organic molecules. The general formula for an oxime is $R_1R_2C=N-O-H$. In an aldoxime, the R1 group is an organic side-chain and R2 may be hydrogen, while in a ketoxime the R2 group comprises another organic functional group.

In various aspects, the plurality of oxime functional groups may comprise at least one bis-pyridinium oxime. For example, the plurality of oxime functional groups may comprise at least one of trimedoxime bromide (TMB-4, also known as dipyroxime), 1,1'1Methylenebis[4-[(hydroxyimino)methyl]-pyridinium dibromide (MMB-4), or combinations thereof.

In various aspects, the at least one polymer covalently conjugated to the esterase forms a long lived covalent conjugate. The number of polymers covalently conjugated to the esterase may include from about 80% to about 100% of the sites available for covalent attachment within the active site of the esterase. For example, the number of polymers covalently conjugated to the esterase may include from about 85% to about 95%, from about 90% to about 95%, or for any range subsumed therein, For example, from about 84% to about 96% of the sites available for covalent attachment within the active site of the esterase.

In various aspects, the number of polymers covalently conjugated to the esterase may be limited by the number of lysine residues exposed to the surface of the enzyme active site. In various aspects, the number of polymers may be bound to about 85%, about 90%, about 95%, or up to 100% of the surface lysine residues of the enzyme active site. Further polymers may be bound to other surface residues of the enzyme. In various aspects, the number of polymers covalently conjugated to the esterase may be limited to a range of about 90% to about 95% for the esterase polymer conjugate to maintain a level of enzyme activity substantially similar to or substantially equal to that of a native enzyme. For example, it has been found that too many polymers bound to the enzyme may diminish enzyme activity. Typically, as many as about 95% of the surface residues (e.g., lysine residues) may be attached to a polymer without loss of enzyme activity.

In various aspects, the covalent attachment of multiple polymers onto the surface of the enzyme active site provides for delayed clearance from the body. For example, the long lived esterase polymer conjugate may remain within circulation in the body of a mammalian recipient thereof for more than about one day, for more than about 5 days, for more than about 1 week, for more than about 2 weeks, for more than about 3 weeks, or for more than about 1 month. In various aspects, the long lived covalent conjugate is maintained in the body for a time period ranging from more than about one day to less than about one week, from more than about 3 days to less than about two weeks, from more than about one week to less than about three weeks, or for more than about two weeks to less than about one month, or for more than about one month, for any sub-range subsumed therein, such as for more than about 2 days to less than one week.

In various aspects, the at least one polymer may comprise at least one environmentally responsive monomer. Environmentally responsive monomers may change conformation, charge, or physical structure in response to a stimulus in the proximate environment of the monomer. For example, and as shown in Table 3, the at least one polymer may comprise at least one of poly(N-isopropylacrylamide), poly(oligo(ethylene glycol) methyl ether methacrylate), poly(sulfobetaine methacrylate), poly(N,N, dimethylaminoethyl methacrylate), poly((meth)acrylate), or the like, or combinations thereof.

In various aspects, the esterase polymer conjugate composition may comprise at least one polymer exhibiting a polymer length ranging from a minimum of at least 2 monomer repeats to about 1000 monomer repeats. For example, the polymer length may range from a minimum of at least 5 monomer repeats to about 750 monomer repeats, from a minimum of at least 25 monomer repeats to about 500 monomer repeats, from a minimum of at least 100 monomer repeats to about 250 monomer repeats, or for any range subsumed therein, For example, from a minimum of 10 monomer repeats to about 900 monomer repeats. The only upper limit on the number or length of monomers is that number or length that will avoid hindering contact of the oxime functional group or groups sufficient to interact with the active site of the enzyme for neutralization of the inhibiting moiety.

In various aspects, the esterase polymer conjugate composition may comprise macromolecules composed of more than one monomeric repeating unit, or co-polymers. In various aspects, the esterase polymer conjugate may comprise at least one polymer that is a co-polymer comprising at least two different monomers, wherein at least one monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and the like, and combinations thereof.

In addition, the co-polymer of the esterase polymer conjugate may comprise at least two different monomers, wherein at least one monomer may comprise a varied topology from at least one different monomer of the co-polymer. More specifically, the varied topology of the at least one monomer may include block, random, star, end-functional, or in-chain functional co-polymer topology. For example, at least one monomer of the co-polymer may include at least one monomer of a di-block topology. The co-polymers, monomers for di-block formation, monomers including an end functional group, or in-chain functional co-polymers may be synthesized utilizing the materials and methods described in U.S. Pat. No. 5,789,487 to Matyjaszewski et al, U.S. Pat. No. 6,624,263 to Matyjaszewski et al, U.S. Patent Application Publication No. 2009/0171024 to Jakubowski et al., and Matyjaszewski, K, and Davis, T. P., ed., Handbook of Radical Polymerization, John Wiley and Sons, Inc., Hoboken, N.J. (2002) are incorporated herein by reference in their entirety, the patents and patent applications including their specifications, drawings, claims and abstracts.

In various aspects, the esterase polymer conjugate may include a plurality of polymers each covalently conjugated to the esterase, each polymer comprising a plurality of monomer units wherein at least one said monomer unit comprises an oxime functional group and wherein a plurality of monomer units of each polymer comprises an oxime functional group. In various aspects, a plurality of monomer units of each polymer of the plurality of polymers may comprise an oxime functional group. In various aspects, the plurality of polymers may comprise co-polymers wherein each co-polymer may include at least two different monomers in which at least one monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and the like, and combinations thereof.

Where the esterase polymer conjugate comprises a co-polymer, the co-polymer may comprise a member of the group consisting of a statistical co-polymer, a random co-polymer, an alternating co-polymer, a block co-polymer, a di-block co-polymer, a tri-block co-polymer, a graft co-polymer, a multiple-block co-polymer, or the like, or combinations thereof.

In various aspects, the esterase polymer conjugate may comprise a plurality of polymers each covalently conjugated to the esterase and each polymer may comprise a plurality of monomer units wherein at least one said monomer unit comprises an oxime functional group and the plurality of polymers comprises a plurality of co-polymers and a plurality of homopolymers. Further, each co-polymer of the plurality of co-polymers may comprise at least two different monomers, wherein at least one monomer comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, Clickable azide monomers, and the like, and combinations thereof. In addition, each homopolymer of the plurality of homopolymers comprises a member selected from the group consisting of aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol)

methyl ether methacrylate, 2-PAM monomers, 4-PAM monomers, Clickable azide monomers, and the like, and combinations thereof.

In various aspects, a composition may comprise a bioconjugate composition formed through a stable covalent link between two biomolecules. The bioconjugate composition may comprise an esterase and at least one polymer covalently conjugated to the esterase. The esterase of the bioconjugate composition may comprise any of the esterases (e.g., acetylcholinesterase, cholinesterase, etc.) described for the esterase polymer composition as described herein. In various aspects, the esterase of the bioconjugate composition may comprise chymotrypsin. The bioconjugate composition may further comprise at least one polymer covalently conjugated to the esterase. The at least one polymer may comprise a plurality of oxime functional groups and at least one oxime functional group of the plurality of oxime functional groups is positioned to react, in use, with a phosphoryl functional group when an inhibitor having a phosphoryl functional group attaches to an active site of the esterase.

In various aspects, the bioconjugate composition may include at least one polymer. For example, the bioconjugate composition may comprise at least one polymer comprising a flexibility sufficient to react, in use, with a phosphoryl functional group when an inhibitor having a phosphoryl functional group attaches to the active site of the esterase. In various embodiments, the bioconjugate composition may include any of the polymers disclosed herein.

In various aspects, the bioconjugate composition may include functional groups. More specifically, the bioconjugate composition may include at least one oxime functional group selected from any of the oxime functional groups described herein.

In various aspects, the bioconjugate composition may include at least one monomer. Specifically, the bioconjugate composition monomer may include any of the monomers described herein. For example, the bioconjugate composition may include at least one of any of the environmentally responsive monomers as described herein.

In various aspects, the bioconjugate composition may serve as a drug delivery system. More specifically the bioconjugate composition may comprise a drug delivery system for polymeric antitoxins. For example, the bioconjugate composition may protect polymeric antitoxins such as polyoximes from clearance from the body and degradation forming a long lived covalent conjugate that is maintained in the body for time periods the same or similar to those described for the esterase polymer conjugate.

In various aspects, the bioconjugate composition may include at least one polymer, the at least one polymer including a polymer length that is the same or similar to that described with respect to the esterase polymer conjugate.

In various aspects, the at least one polymer of the bioconjugate composition may comprise a co-polymer. For example, the at least one polymer may include at least two different monomers as described herein. In various aspects, the bioconjugate composition may include a plurality of polymers each covalently conjugated to the esterase. More specifically, each polymer may include a plurality of monomer units or monomers as described herein. In various aspects, the plurality of polymers may include co-polymers. For example, the co-polymers may include at least two different monomers as described herein.

In various aspects, the plurality of polymers may include a plurality of co-polymers and a plurality of homopolymers. More specifically, each co-polymer and each homopolymer may include at least one of the monomers as described herein.

In various aspects, the bioconjugate composition may interact with and therefore at certain times as it functions, the bioconjugate composition may be bound to an inhibitor. For example, the bioconjugate composition may interact with and include VX, Sarin, Soman, DFP, Paraoxon, Parathion, or the like, or combinations.

In various aspects, a method is provided including administering a bioscavenger to an individual suffering from toxin exposure. More specifically, the toxin exposure may be due to exposure of the individual to an organophosphate toxin, a nerve agent, a neurotoxin. The bioscavenger may include at least one polymer attached to an enzyme. For example, the at least one polymer may include a plurality of oxime groups as described herein covalently bound to an esterase. In various aspects, upon exposure of the bioscavenger to an OP toxin the method includes reacting at least one of a plurality of oxime functional groups with at least one covalently inhibited residue of an esterase to detoxify and regenerate the bioscavenger.

In various aspects, the method may include administering the bioscavenger to an individual person or to a mammalian individual.

In various aspects, the plurality of oxime functional groups of the bioscavenger conjugate may include an oxime functional group positioned to exert a nucleophilic attack on an inhibitor, when in use, the inhibitor attaches to an active site of the esterase. For example, the method may include an oxime functional group positioned to exert a nucleophilic attack on a phosphoryl functional group inhibiting the active site of the esterase, resulting in the removal of the phosphoryl functional group from the active site.

In various aspects, the method of administering a bioscavenger to an individual suffering from OP toxin exposure may include administering a long lived covalent enzyme polymer conjugate that is maintained in the body for time periods the same or similar to those described for the esterase polymer conjugate.

In various aspects, the esterase of the bioscavenger conjugate may comprise any of the esterases described for the esterase polymer composition as described herein. For example, the esterase of the bioscavenger conjugate may comprise chymotrypsin, acetylcholinesterase, cholinesterase, etc.

In various aspects, the administered bioscavenger may include a plurality of oxime functional groups. For example, the administered bioscavenger may include at least one oxime functional group selected from any of the oxime functional groups described herein. In various aspects, the administered bioscavenger may include at least one polymer, the at least one polymer including a polymer length that is the same or similar to that described with respect to the esterase polymer conjugate.

In various aspects, the administered bioscavenger may include at least one monomer. Specifically, the bioconjugate composition monomer may include any of the monomers described herein. For example, the administered bioscavenger may include at least one of any of the environmentally responsive monomers as described herein.

In various aspects, the at least one polymer of the administered bioscavenger may comprise a co-polymer. For example, the at least one polymer may include at least two different monomers as described herein. In various aspects, the administered bioscavenger may include a plurality of polymers each covalently conjugated to the esterase. More specifically, each polymer may include a plurality of monomer units or monomers as described herein.

In various aspects, the plurality of polymers may include co-polymers. For example, the co-polymers may include at least two different monomers as described herein. In various aspects, the plurality of polymers may include a plurality of co-polymers and a plurality of homopolymers. More specifically, each co-polymer and each homopolymer may include at least one of the monomers as described herein.

In various aspects, a bioscavenger may comprise at least one polymer covalently conjugated to an esterase. The esterase of the bioscavenger may comprise any of the esterases (e.g., acetylcholinesterase, cholinesterase, etc.) described for the esterase polymer composition as described herein. In various aspects, the esterase of the bioscavenger may comprise chymotrypsin.

In various aspects, the bioscavenger may comprise at least one polymer covalently conjugated to the esterase. The at least one polymer may comprise a plurality of oxime functional groups and at least one oxime functional group of the plurality of oxime functional groups is positioned to exert a nucleophilic attack on a phosphoryl functional group when, in use, a phosphoryl functional group is covalently attached to an active site of the esterase effecting removal of the phosphoryl functional group from the active site and regeneration of the bioscavenger. In various aspects, the at least one oxime functional group comprises an oxime functional group positioned to exert a nucleophilic attack on a phosphoryl functional group when, in use, an inhibitor having a phosphoryl functional group attaches to an active site of the esterase. More specifically the nucleophilic attack results in the removal of the phosphoryl functional group from the active site.

In various aspects, the bioscavenger may serve as a drug delivery system. More specifically the bioconjugate composition may comprise a drug delivery system for polymeric antitoxins. For example, the bioscavenger may protect polymeric antitoxins such as oximes from clearance from the body and degradation forming a long lived covalent conjugate that is maintained in the body for time periods the same or similar to those described for the esterase polymer conjugate.

In various aspects, the bioscavenger may include functional groups. More specifically, the bioscavenger may include at least one oxime functional group selected from any of the oxime functional groups described herein.

In various aspects, the bioscavenger may include at least one polymer, the at least one polymer including a polymer length that is the same or similar to that described with respect to the esterase polymer conjugate.

In various aspects, the bioscavenger may include at least one monomer. Specifically, the bioscavenger monomer may include any of the monomers described herein. For example, the bioscavenger may include at least one of any of the environmentally responsive monomers as described herein.

In various aspects, the at least one polymer of the bioscavenger may comprise a co-polymer. For example, the at least one polymer may include at least two different monomers as described herein. In various aspects, the bioconjugate composition may include a plurality of polymers each covalently conjugated to the esterase. More specifically, each polymer may include a plurality of monomer units or monomers as described herein. In various aspects, the plurality of polymers may include co-polymers. For example, the co-polymers may include at least two different monomers as described herein. In various aspects, the plurality of polymers may include a plurality of co-polymers and a plurality of homopolymers. More specifically, each co-polymer and each homopolymer may include at least two different monomers as described herein.

The result of this investigation is a broad spectrum antidote that can be used as an internal therapeutic for OP toxins primarily from pesticides and chemical weapons. The work of engineering an optimized polymer-protein conjugate uses the AChE-poly-2-PAM conjugate described above as the starting point.

Example 1

Oxime Polymer Synthesis

The synthesis of an acrylate polymer 3,4-dimethoxy-N-methylamphetamine (DMMA) 4-pyridine aldoxime (4-PAM) random copolymer as part of a multicomponent electrospun polyurethane material has been reported. Amitai G, Murata H, Andersen J D, Koepsel R R, Russell A J., Decontamination of chemical and biological warfare agents with a single multi-functional material, *Biomaterials*, 31(15):4417-25 (2010). This water soluble 4-PAM co-polymer demonstrated a dose-response pH dependent detoxification of diisopropyl fluorophosphate (DFP). The hydroxyl-ethyl-4-PAM residue was bound to the co-polymer backbone by an ester bond allowing its controlled release from the polymer. The released hydroxyl-ethyl-4-PAM was shown to reactivate DFP inhibited AChE at a similar rate as the antidote oxime 4-PAM. The same synthetic process was used to synthesize a 2-PAM polymer (see FIGS. 3A-3E). The polymer was synthesized by thermo polymerization as a random co-polymer of dimethyl acrylamide (DMAA) and methacrylbromide (MA-Br) (see FIG. 3A). The polymer was then quaternized with 2-pyridine aldoxime (see FIG. 3C) and modified to contain a terminal NHS moiety (see FIG. 3E).

Figure 3A:
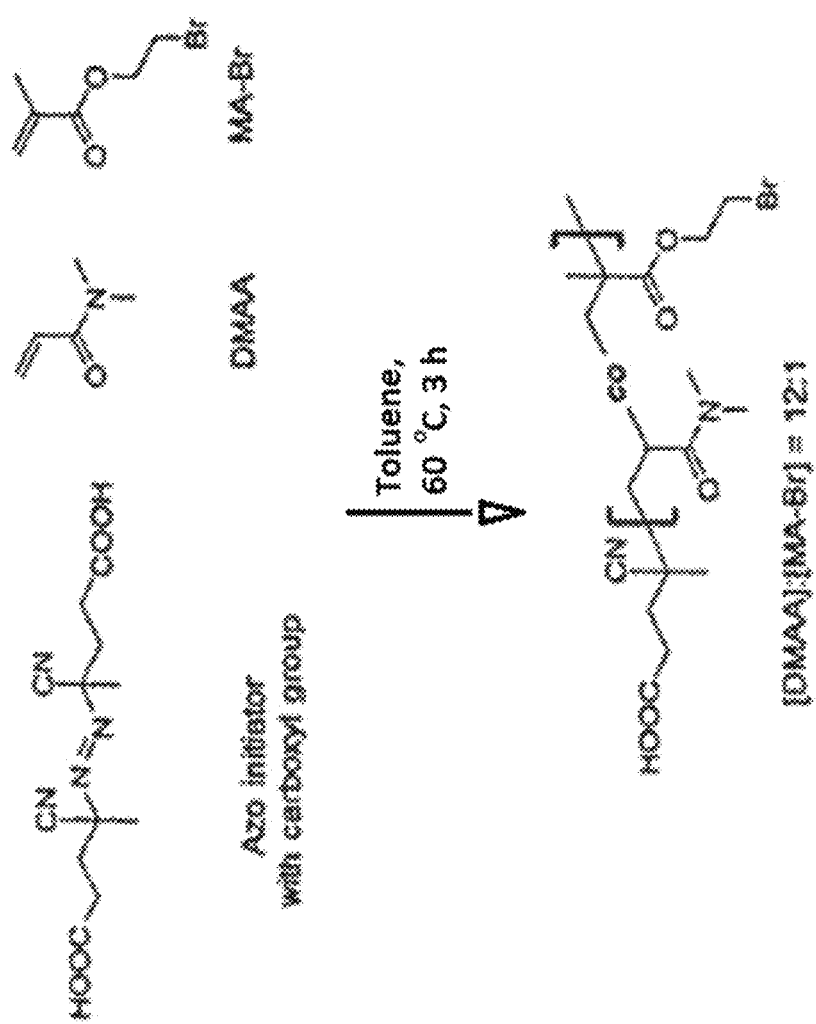
Figure 3B:
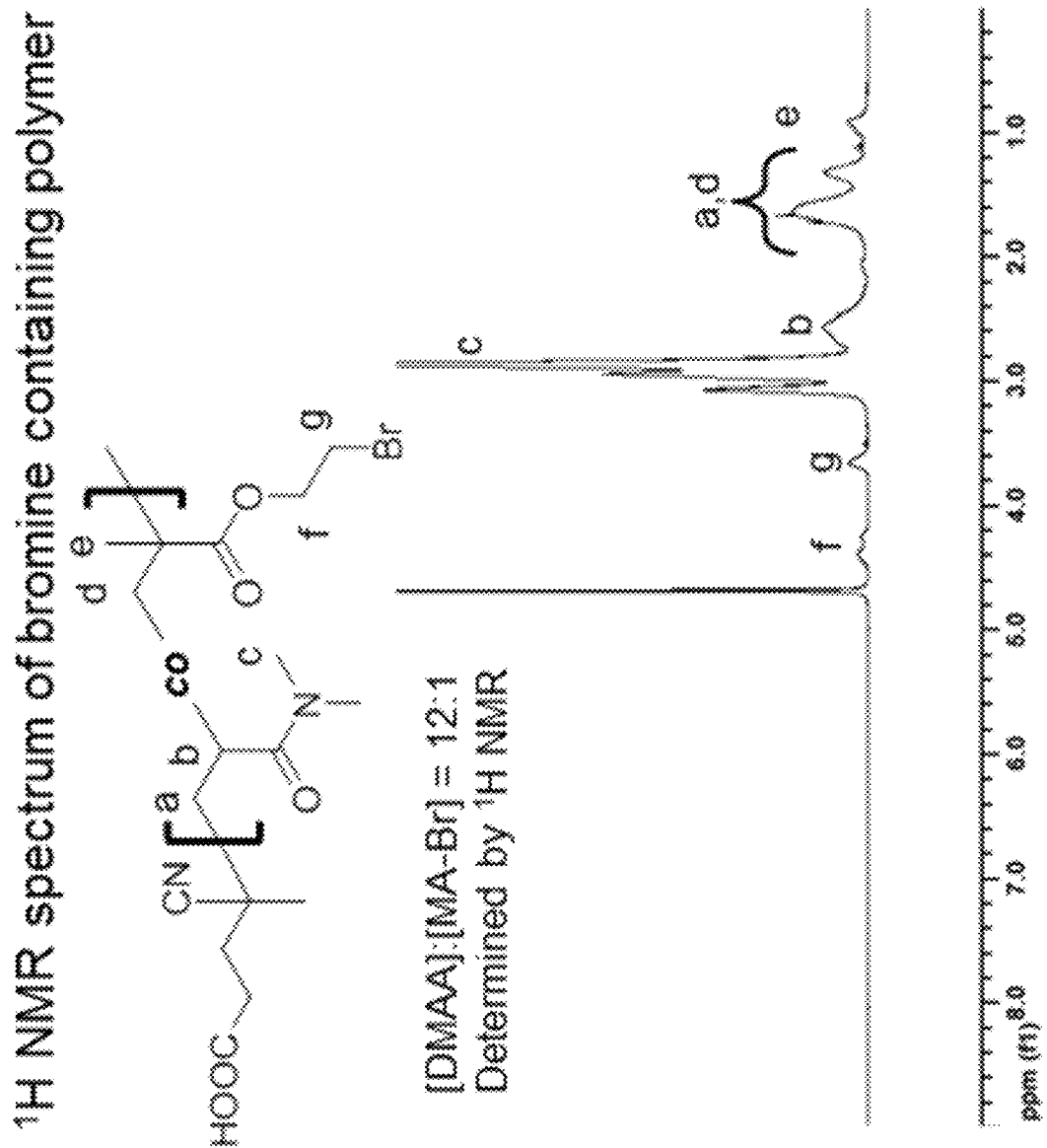

FIG. 3A illustrates a schematic of the preparation of a bromine containing polymer the first step in the synthesis of the first AChE-polymer conjugate. Preparation of the bromine containing polymer included the following materials and methods:

Monomers DMAA (4.0 mL, 38.8 mmol), and 2-bromoethyl methacrylate (750 mg, 3.9 mmol) were placed in a polymerization tube and covered with 4,4'-azobis(4-cyanovaleric acid) (140 mg, 0.5 mmol) as an initiator and 50 mL of Toluene. The monomer solutions were degassed by five freeze-pump-thaw cycles and then heated to 60° C. for 3 h. The resulting mixture was precipitated with diethyl ether (500 mL). The ether-insoluble part was filtrated off and dried overnight in vacuo: yield 2.8 g (73%), number average molecular weights (Mn) and the distributions (Mw/Mn) of the obtained polymer was estimated by gel permeation chromatography (GPC) on a Waters 600E Series with a data processor, equipped with three polystyrene columns (Waters styragel HR1, HR2 and HR4), using DMF with LiBr (50 mM) as an eluent at a flow rate of 1.0 mL/min, polymethylmethacrylate calibration, and a refractive index (RI) detector resulting in a Mn of 29,400 g/mol and the distributions of (Mw/Mn) 3.99. The chemical structure and concentration of bromine groups of the obtained polymer was determined by $^1$H NMR spectra (see FIG. 3B), which was recorded on a Bruker Avance (300 MHz) spectrometer in DMSO-d6. When this polymer was grafted to AChE the resulting conjugate had an average of 6 of the 13 accessible lysines conjugated to the enzyme. This AChE poly-2-PAM covalent conjugate was designed to demonstrate the effect of oximes conjugated to the enzyme surface.

Figure 3C:
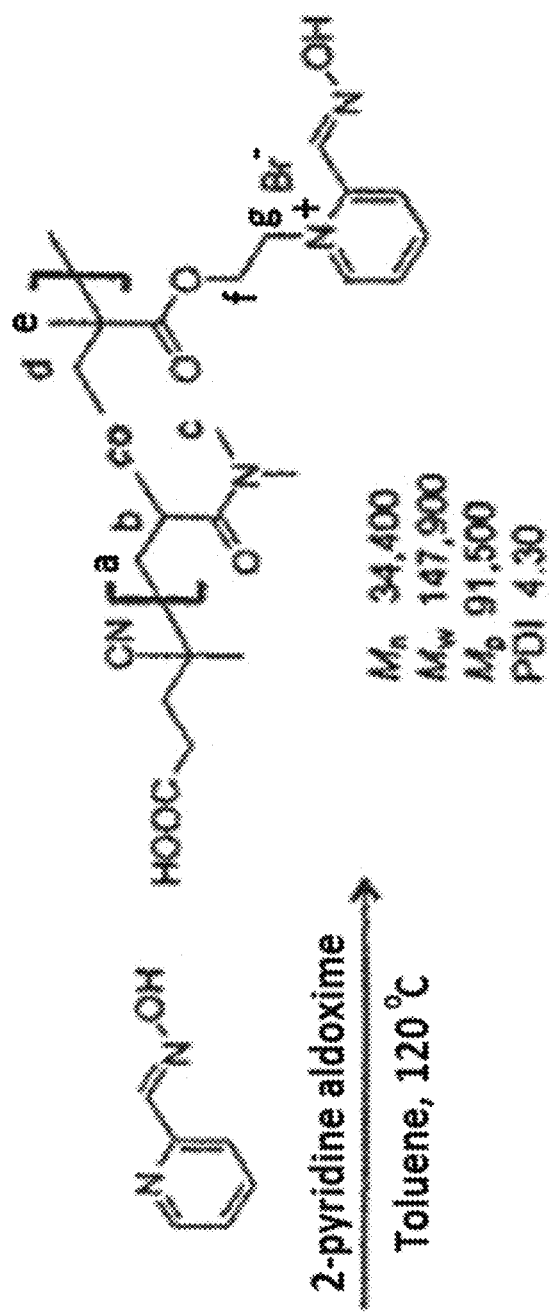

FIG. 3C is the chemical reaction of the quaternization reaction with 2-PAM. The quaternization reaction with 2-PAM procedure included the following materials and methods: The bromine containing polymer of FIGS. 3A and 3B (2.9 g, 2.1 mmol of bromine), syn-2-pyridinealdoxime (650 mg, 5.3 mmol) and toluene were placed into a flask and refluxed at 120° C. overnight. After cooling down, the mixture was precipitated in diethyl ether and filtered. The product was purified by decantation with acetone/diethyl ether several times. The obtained polymer was dried in vacuo: yield 2.5 g, the number average molecular weights (Mn) and the distributions (Mw/Mn) of the obtained polymer was estimated by GPC resulting in a Mn of 34,400 and the distributions of (Mw/Mn) 4.30. The chemical structure and concentration of 2-PAM groups of the obtained polymer was determined by $^1$H NMR spectra as shown in FIG. 3D.

Figure 3D:
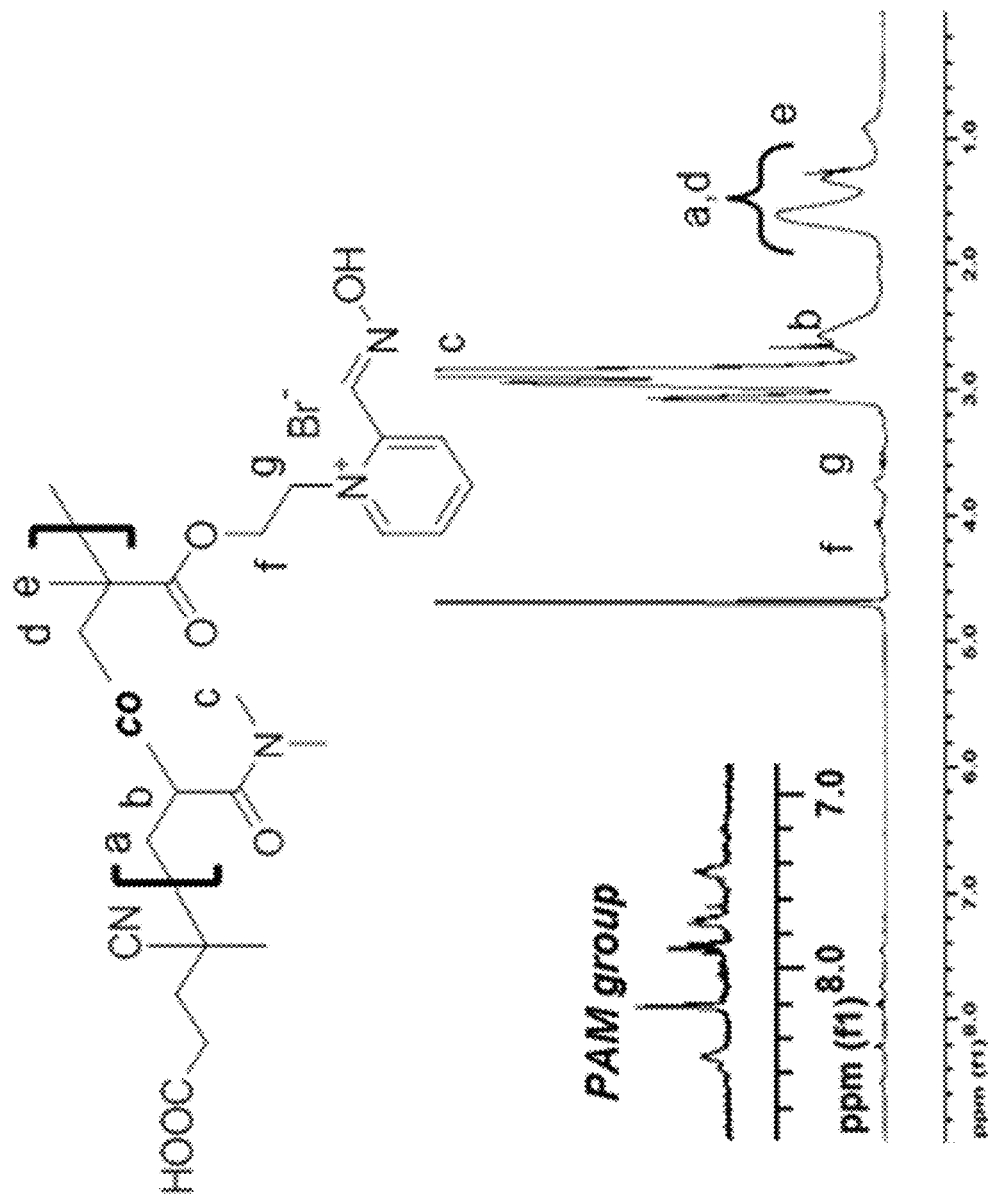
Figure 3E:
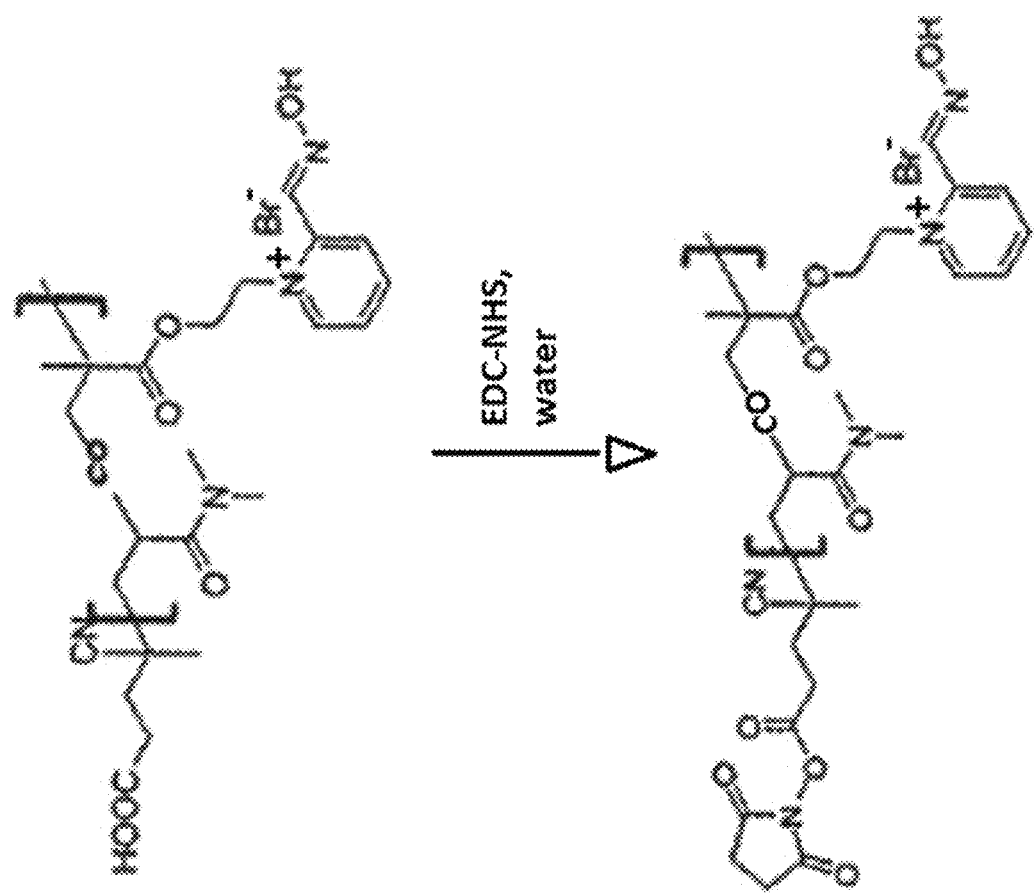

FIG. 3E illustrates the chemical generation of an N-oxysuccinimide ester group on the 2-PAM polymer shown in FIGS. 3C and 3D. Preparation of the generation of N-oxysuccinimide ester group on the 2-PAM polymer included the following materials and methods: Ethyl(dimethylaminopropyl) carbodiimide hydrochloride (EDC.HCl) (39 mg, 0.2 mmol) and N-hydroxysuccinimide (NHS) (24 mg, 0.2 mmol) were added in a solution of the 2-PAM polymer (680 mg, 0.02 mmol of —COOH end group) in deionized water (20 mL) and stirred at room temperature for 30 min. The obtained polymer was isolated by dialysis using a molecular weight cut off 1,000 dialysis tube in the refrigerator (4° C.), then lyophilized.

AChE-Polymer Conjugates

Figure 3F:
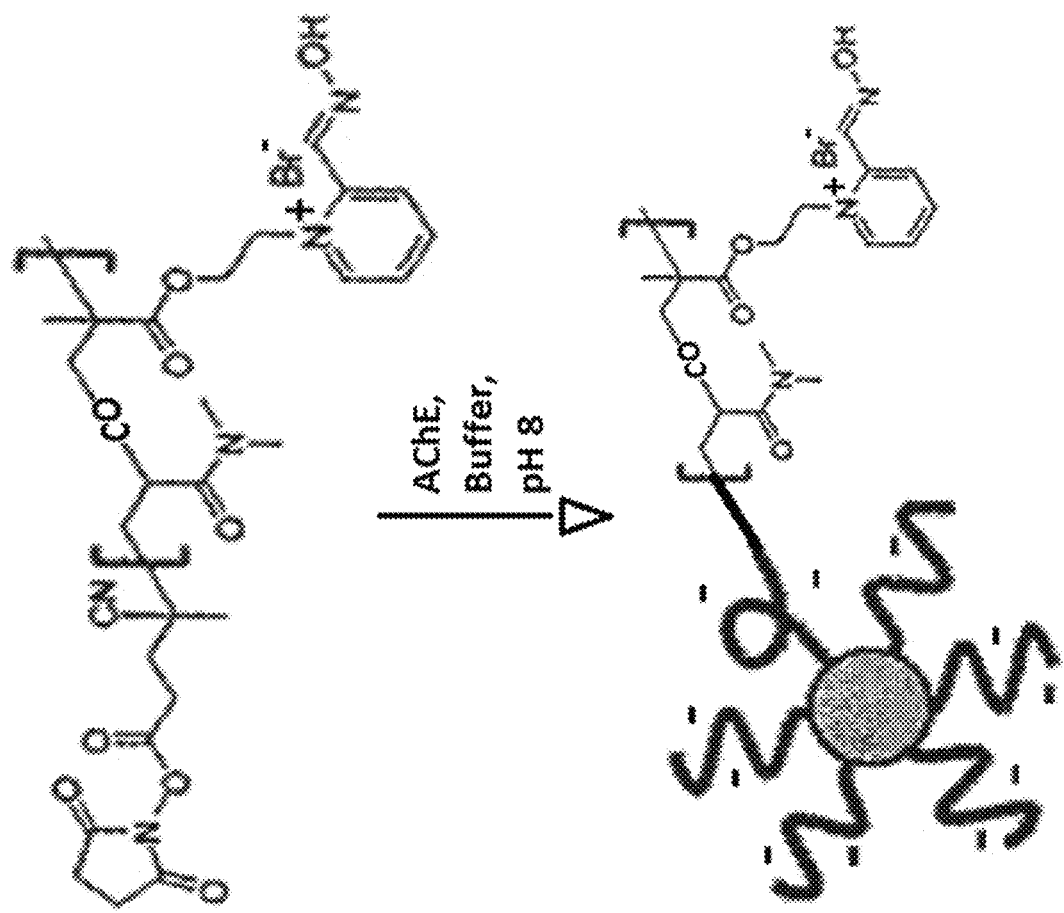

An AChE-polymer conjugate was synthesized including the 2-PAM containing polymer as shown in FIG. 3E synthesized using a "grafted to" approach (see FIG. 3F). FIG. 3F illustrates a schematic of the conjugation of the 2-PAM polymer shown in FIG. 3E with AChE. Preparation of the conjugation of the 2-PAM polymer with AChE included the following materials and methods: Polymer from the generation of the N-oxysuccinimide ester group on the 2-PAM group of FIG. 3E (210 mg, 6.2 µmol) was added in a solution of AChE (from Electrophorus electricus (electric eel), 10 mg, 3.1 µmol of amine groups) in 100 mM sodium phosphate buffer (10 mL, pH 8.0) and stirred at 4° C. overnight. The obtained AChE-2-PAM conjugate was isolated by dialysis using a molecular weight cut off 50 kDa dialysis tube in the refrigerator (4° C.), overnight, then lyophilized. 10 wt % of AChE in the conjugate was found by bicinchoninic acid (BCA) protein assay and the polymer grafting density was determined by fluorescamine amine assay, respectively.

A BCA protein assay was used to determine the protein percent composition of AChE within the AChE-2-PAM conjugate using the following materials and methods: Solutions (25 µL each) of varying concentrations of native AChE (0.05-1.0 mg/mL; used for preparation of a standard curve) and 1.0 mg/mL of AChE-2-PAM polymer conjugate in deionized water were mixed with 1 mL of BCA solution (15 mL of Bicinchoninic Acid solution (Sigma-Aldrich) with 300 µL, of Copper (II) sulfate solution (Sigma-Aldrich)). The solution was incubated at 60° C. for 15 min. Absorbance of the solution at 562 nm was measured by UV/VIS spectrometer. Protein concentration in the conjugate was estimated by comparison to native AChE standards.

A fluorescamine amine assay was used to determine the number of initiators or polymers attached to the enzyme surface using fluorescamine. In a fluorescamine amine assay the fluorescamine molecule reacts with primary amines (lysines) to form a fluorophore with an excitation of 365 nm and an emission of 470 nm (see below). Equal molar solutions (0.1 M phosphate buffer pH 8) of native enzyme and modified enzyme (at concentrations approximating 1 mg/ml) were prepared. Fluorescamine was added in dimethyl sulfoxide (DMSO) to 1 mg/ml final concentration. The sample was incubated for 15 minutes at 25° C. and fluorescence was measured at 470 nm.

Example 2

Figure 4A:
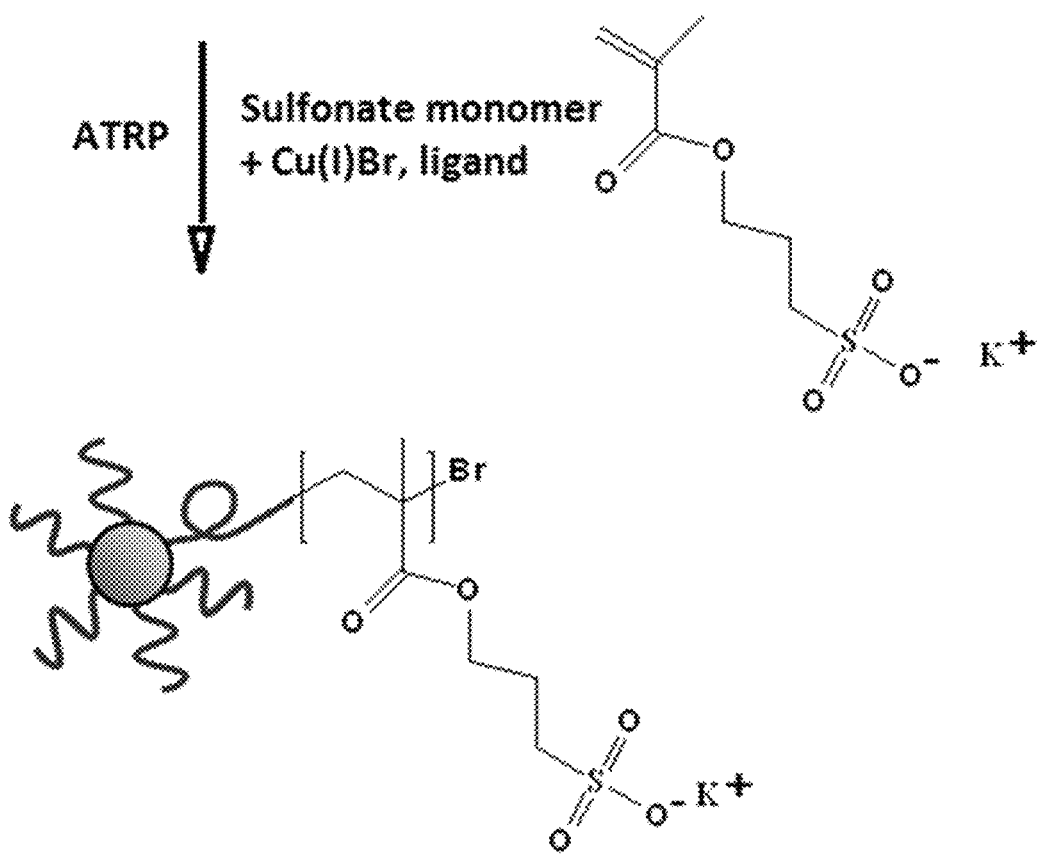
Figure 4B:
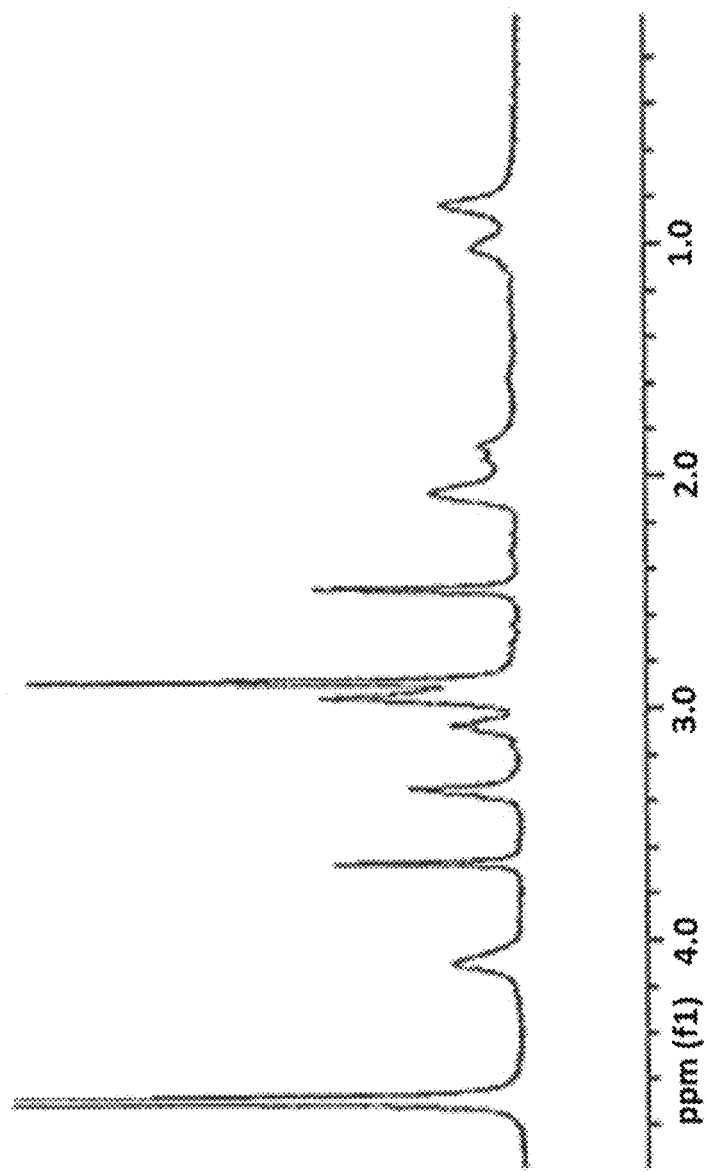

A second AChE-polymer conjugate was synthesized including a sulfonate monomer using the "grafted from" approach as shown in FIGS. 4A and 4B. The AChE-polymer conjugate was synthesized directly from the surface of AChE by ATRP including a sulfonate monomer. The synthesis of the second AChE-polymer conjugate included the following materials and methods:

AChE (from Electrophorus electricus (electric eel), 23 mg, 7.2 µmol of amine groups) was dissolved in 100 mM sodium phosphate buffer (20 mL, pH 8.0) at 0° C. After adding N-2-bromo-2-methylpropionyl-β-alanine N-oxysuccinimide ester (7 mg, 20 µmol), the mixture was stirred in a refrigerator (4° C.) for 3 h and the AChE-initiator conjugate was isolated by dialysis using a 50 kDa molecular weight cut off dialysis tube in deionized water in a refrigerator (4° C.) for 24 h and then lyophilized. 60% of the AChE surface lysines was reacted with the NHS functionalized ATRP initiator, which was estimated by TNBSA (2,4,6-Trinitrobenzene sulfonic acid) amine assay. To determine the percent of AChE surface lysines reacted with the NHS functionalized ATRP initiator the TNBSA amine assay was performed using the following materials and methods:

Solutions (500 µLeach) of varying concentrations of native AChE (0.1-1.0 mg/mL; used for preparation of a standard curve) and 1.0 mg/mL of AChE-ATRP initiator conjugate in 100 mM sodium phosphate buffer (pH 8.5) were mixed with 250 µL of TNBS solution (20 µl, of 5% TNBS stock solution (Sigma-Aldrich) with 10 mL of 100 mM sodium phosphate buffer (pH8.5). The solution was incubated at 37° C. for 2 h. 125 µL of 1 N HCl aq. and 250 µL of water were added to each sample to stop and stabilize the reaction. The absorbance of the solution at 345 nm was measured by ultraviolet-visible spectroscopy using polymethyl methacrylate (PMMA) cuvettes. Concentration of unreacted primary amines on the AChE-ATRP initiator conjugates was estimated by comparison to native AChE standards.

As shown in the schematic of FIG. 4A, a solution of 3-sulfopropyl methacrylate potassium salt (22 mg, 89 µmop and AChE-initiator conjugate (5 mg, 0.89 µmol of initiator groups) in 50 mM sodium phosphate buffer (10 mL, pH 7.4) was sealed and bubbled with nitrogen for 50 min. Deoxygenated catalyst solutions of HMTETA (1,1,4,7,10,10-Hexamethyltriethylenetetramine, 1.0 µL, 3.6 µmol) and Cu(I)Br (0.6 mg, 3.6 µmop in deionized water (1 mL) was then added to the conjugation reactor under nitrogen bubbling. The mixture was sealed and stirred in a refrigerator (4° C.) for 18 h. AChE-sulfonate polymer conjugate was isolated by dialysis with a 50 kDa molecular weight cut off dialysis tube in deionized water in a refrigerator (4° C.) for 24 h and then lyophilized. Molecular weight of the AChE-sulfonate polymer conjugate (146 kDa) was estimated by BCA protein assay using the materials and methods described herein.

The AChE-poly-sulfonate conjugate was designed to assess the effect of negative charges on the surface of the enzyme. The synthesized AChE-poly-sulfonate conjugate of FIGS. 4A and 4B had polymer grafted to all 13 available amine groups. The $^1$H NMR spectrum of the AChE-polysulfonate conjugate is shown in FIG. 4B.

Figure 5:
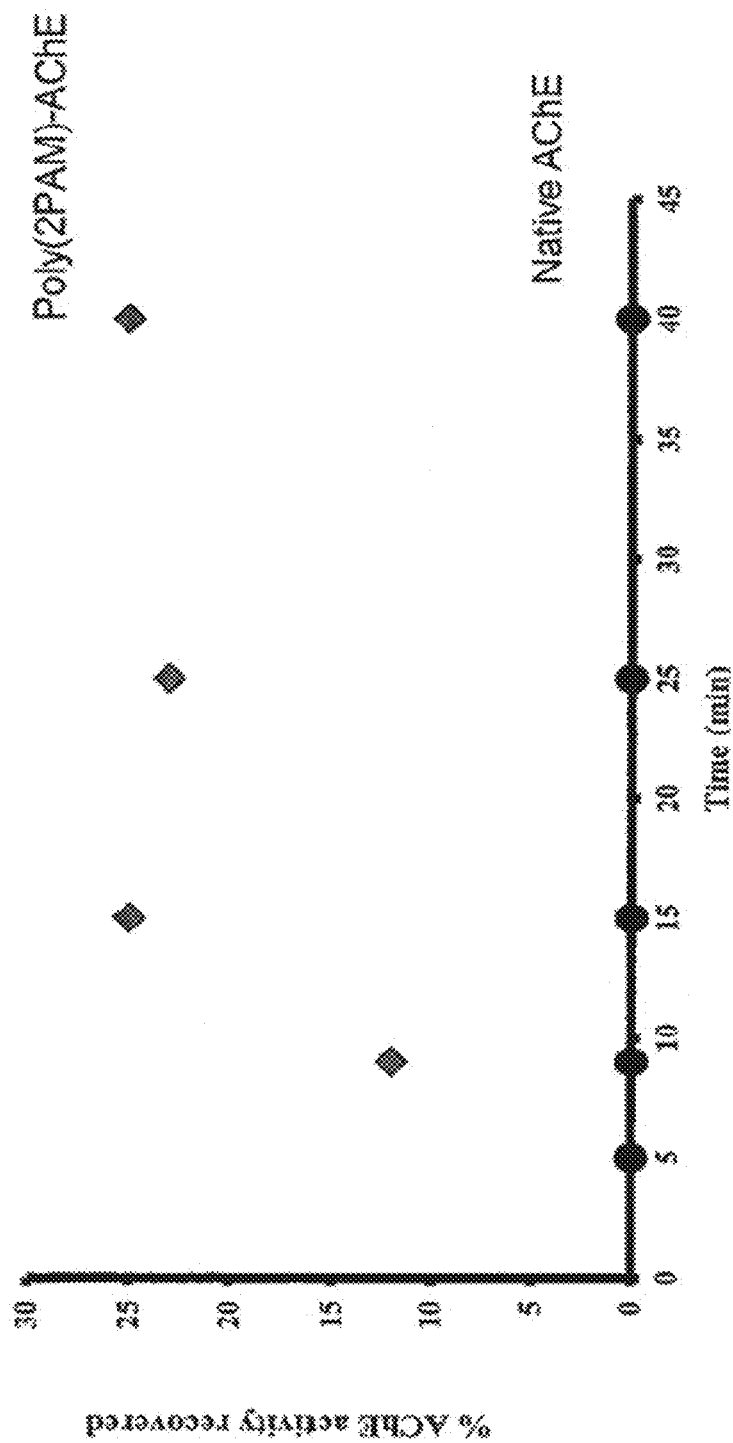

Activity assays of the AChE-poly-2-PAM conjugate and the AChE-poly-sulfonate conjugate showed that the esterase polyoxime covalent conjugate retained upward of 90% of the native activity while the AChE-poly-sulfonate conjugate retained less than 1%. An activity assay was completed on native AChE and the AChE-poly-2-PAM conjugate using the following materials and methods: Native AChE and AChE-poly-2-PAM conjugate (0.4 µM each) were incubated in 1 µM paraoxon until completely inhibited (Native AChE incubated for 10 min, and the AChE-poly-2-PAM conjugate incubated for 15 min). The enzymes were diluted 40 fold into activity buffer (50 mM sodium phosphate pH 7.4, 1 mM acetylthiocholine iodide and 0.74 mM 5,5'-Dithiobis (2-nitrobenzoic acid). Aliquots were tested for activity at the times indicated in the graph of the data as shown in FIG. 5. It is likely that the negatively charged shell generated around the AChE-poly-sulfonate conjugated enzyme was binding the positively charged substrate and limiting access to the active site. It is unlikely, however, that there was a critical lysine that remained unbound as the enzyme-initiator complex retained native activity levels. The activity assay was also completed on native AChE and the AChE-polysulfonate conjugate using the same materials and methods as described above for the native AChE.

Inhibition/reactivation assays were also performed. To achieve enzyme inhibition, the native AChE and the AChE-poly-2-PAM (0.4 µM each) were incubated in 1 µM paraoxon until completely inhibited as described above in the activity assay. Incubation time was 10 minutes for the native AChE and 15 min for the AChE-poly-2-PAM. The enzymes were diluted 40 fold into an activity buffer. Reactivation assays were performed using the following materials and methods: The native AChE and the 2-PAM conjugate ($3.6 \times 10^{-7}$ M) were inhibited with Paraoxon ($1 \times 10^{-6}$ M). Aliquots were sampled out into activity assay buffer containing 50 mM sodium phosphate pH 7.4, 1 mM acetylthiocholine iodide and 0.74 mM 5, 5'-Dithiobis (2-nitrobenzoic acid), and the change in optical density at 412 nm (OD412)/sec was monitored for a decrease in the OD/sec to achieve 90-95% inhibition. The inhibited enzyme was then diluted 1:50 into buffer. Aliquots were sampled out into activity assay buffer. The rate of hydrolysis of substrate was monitored by the increase in absorption at 412 nm.

The behavior of the AChE-poly-sulfonate conjugate in these assays was unremarkable, closely mimicking native enzyme, yet another indication that the conjugation does not modify the enzyme active site. In contrast, the esterase polymer covalent conjugate, AChE poly-2-PAM, showed a five-fold protection from acute inhibition at high paraoxon concentration as a result of delivering the poly-2-PAM polyoxime with the enzyme (see FIG. 5). More importantly, when the inhibited AChE-poly-2-PAM polyoxime conjugate was diluted into buffer it underwent self-reactivation while the native enzyme remained completely inhibited. The rapid initial rate of self-reactivation is similar to that seen when native enzyme is regenerated by free 2-PAM (as discussed in the recent work by Amitai G, Murata H, Andersen J, Koepsel R, Russell A J, Decontamination of chemical and biological warfare agents with a single multifunctional material, *Biomaterials*, 31:4417-4425 (2010). Native enzyme does not self-reactivate or self-regenerate.

The steady state (see FIG. 5) reached after the initial reactivation is likely due to residual paraoxon carried over from the inhibition reaction. These results suggest that the polymeric 2-PAM attached to the esterase enzyme is indeed functioning to self-regenerate esterase activity as intended. The ability of the esterase polymer covalent conjugate, AChE poly-2-PAM, to self-regenerate implies that at least a portion of the oxime residues of the surface attached polymers have access to the active site of the enzyme.

Optimization of the esterase polymer covalent conjugate can include optimization of parameters such as the polymer length, monomer content, the length of the oxime tether, the oxime concentration, and the active oxime identity that can result in a super-scavenger that is very likely catalytic. Suitable local oxime concentrations as effective at the active site of the enzyme may range between about 5 to about 500 oxime functional groups per active site. For example, local oxime concentrations as effective at the active site of the enzyme may range from between about 1 to about 5 oxime functional groups per active site, about 1 to about 10 oxime functional groups per active site, about 5 to about 10 oxime functional groups per active site, about 10 to about 25 oxime functional groups per active site, about 25 to about 100 oxime functional groups per active site, about 100 to about 500 oxime functional groups per active site, or less than about 500 oxime functional groups per active site. Actual oxime concentration per unit volume may range from about 20 mM to about 0.0001 mM, from about 10 mM to about 0.001 mM, from about 5 mM to about 0.01 mM, or from about 1 mM to about 0.1 mM, or for any range subsumed therein, for example, from about 6 mM to about 0.006 mM.

Example 3

Esterase-Polyoxime Conjugate Synthesis Using ATRP

"Grafting from" ATRP has been used to synthesize enzyme-polymer conjugates Murata H, Cummings C S, Koepsel R R, Russell A J, Polymer-Based Protein Engineering Can Rationally Tune Enzyme Activity, pH-Dependence, and Stability, *Biomacromolecules*, 10:14(6):1919-26 (2013); Cummings C, Murata H, Koepsel R, Russell A J, Tailoring enzyme activity and stability using polymer-based protein engineering, *Biomaterials*, 34: 7437-7443 (2013).

A "grafting from" ATRP synthesis of an AChE-PDMAA/poly-2-PAM esterase poly-oxime conjugate was completed as schematically represented in FIGS. 6A-6D using the following materials and methods: AChE (from Electrophorus electricus (electric eel), 20 mg, 6.3 µmol of amine groups) was dissolved in 100 mM sodium phosphate buffer (20 mL, pH 8.0) at 0° C. After adding the N-2-cholopropionyl-β-alanine N-oxysuccinimide ester (5.3 mg, 19 µmol), the mixture was stirred in a refrigerator (4° C.) for 3 hand the AChE-initiator conjugate was isolated by dialysis using a 50 kDa molecular weight cut off dialysis tube in deionized water in a refrigerator (4° C.) for 24 hand then lyophilized. 76% of the AChE surface lysines were reacted with the NHS functionalized ATRP initiator, which was estimated by fluorescamine amine assay as described herein.

Figure 6A:
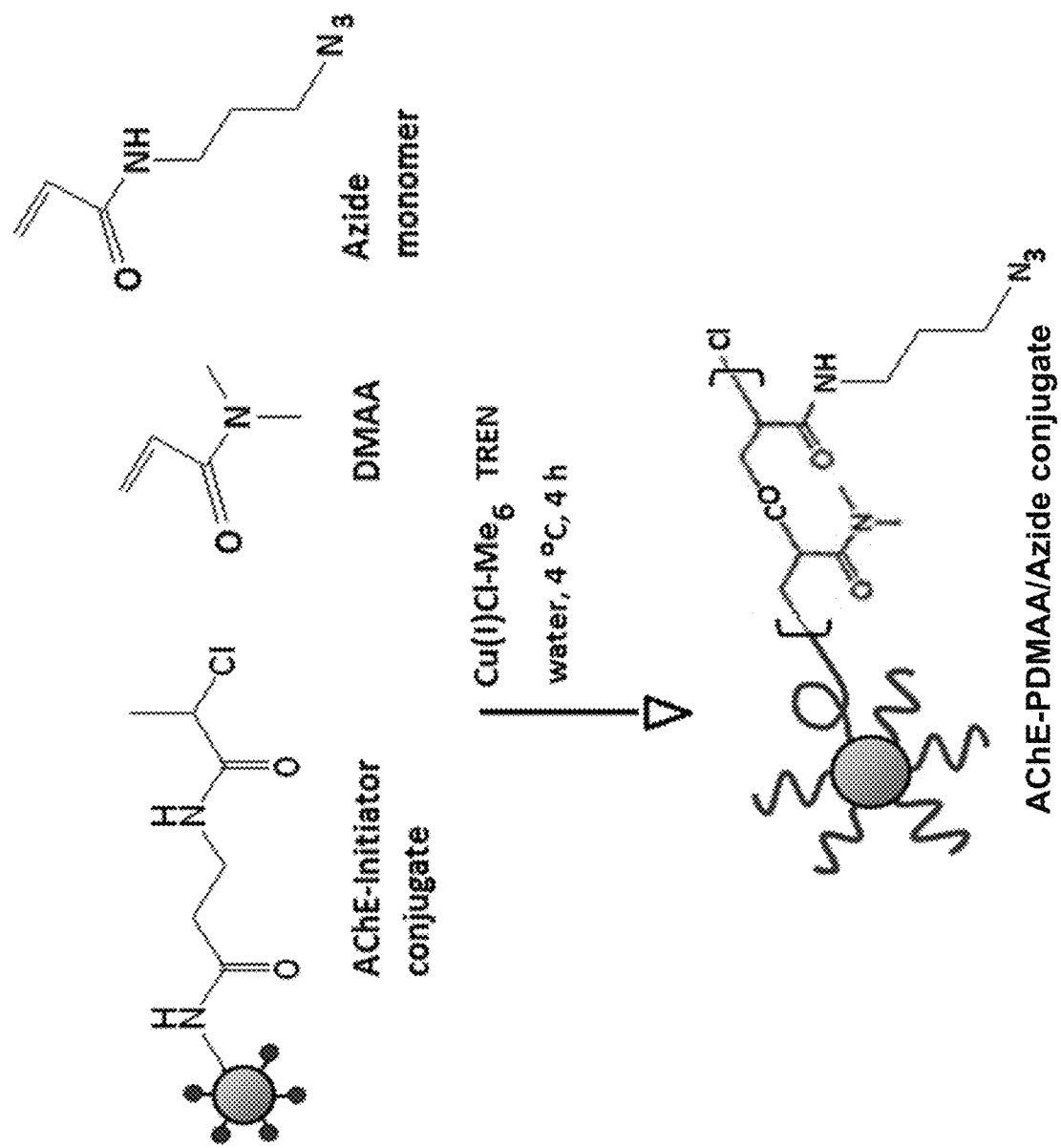

As illustrated in the schematic of FIG. 6A, a solution of DMAA (N,N-dimethyl acrylamide, 48 µL, 450 µmol), N-3-azidopropyl acrylamide (24 mg, 150 µmop and AChE-initiator conjugate (10 mg, 2.3 µmol of initiator groups) in deionized water was sealed and bubbled with nitrogen for 50 min. Deoxygenated catalyst solutions of Me$_6$TREN (Tris[2-(dimethylamino)ethyl]amine, 1.0 µL, 15 µmol) and Cu(I)Cl (1.5 mg, 15 µmol) in deionized water (1 mL) was then added to the conjugation reactor under nitrogen bubbling. The mixture was sealed and stirred in a refrigerator (4° C.) for 18 h. AChE-PDMAA/Azide conjugate was isolated by dialysis with a 50 kDa molecular weight cut off dialysis tube in deionized water in a refrigerator (4° C.) for 24 hand then lyophilized. Molecular weight of the AChE-PDMAA/Azide conjugate (350 kDa) was obtained by BCA protein assay using the BCA materials and methods described herein. The chemical structure of AChE-PDMAA/Azide conjugate in D20 was determined by $^1$H NMR spectrum (see FIG. 6B). Thirty-eight azide groups per grafted polymer chain, (i.e. 730 azide groups on single conjugate molecules) were estimated by $^1$H NMR spectrum.

Figure 6B:
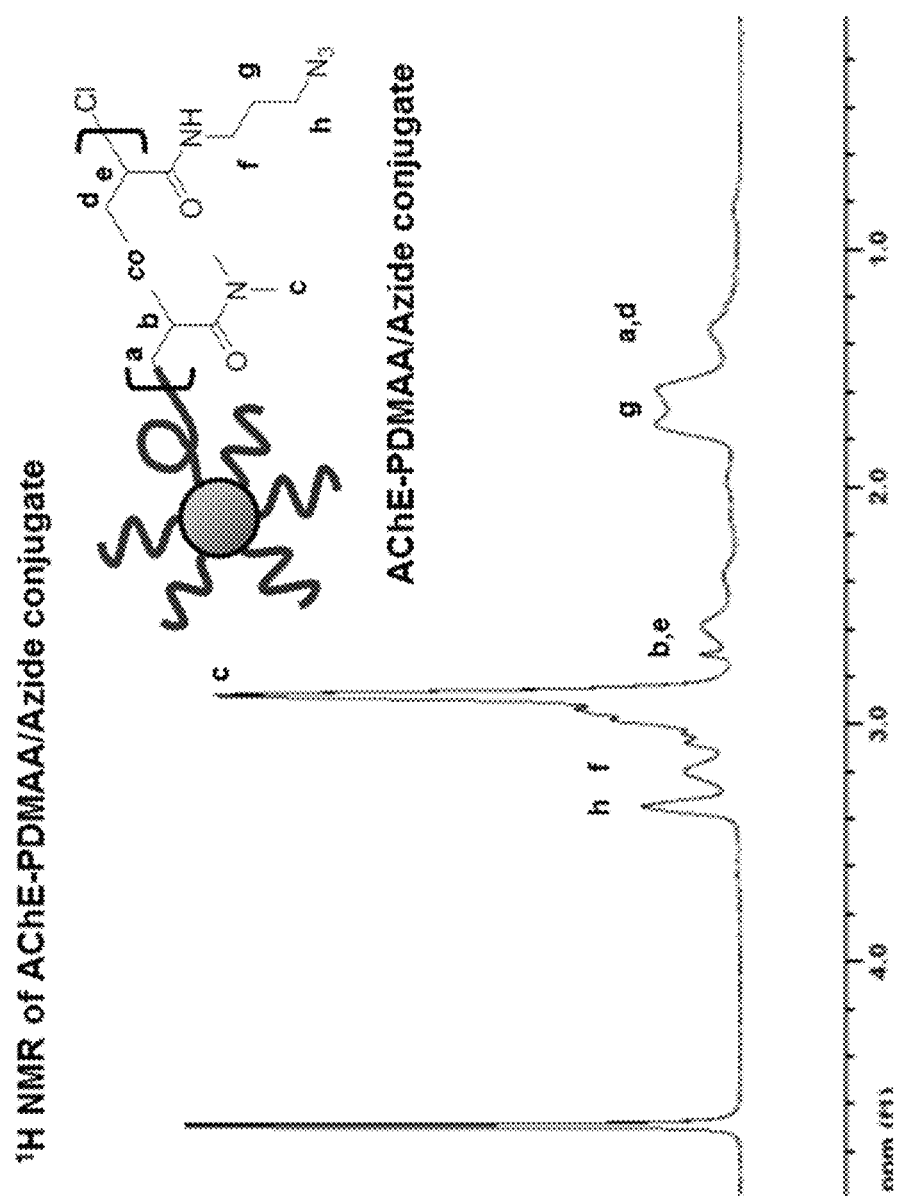
Figure 6C:
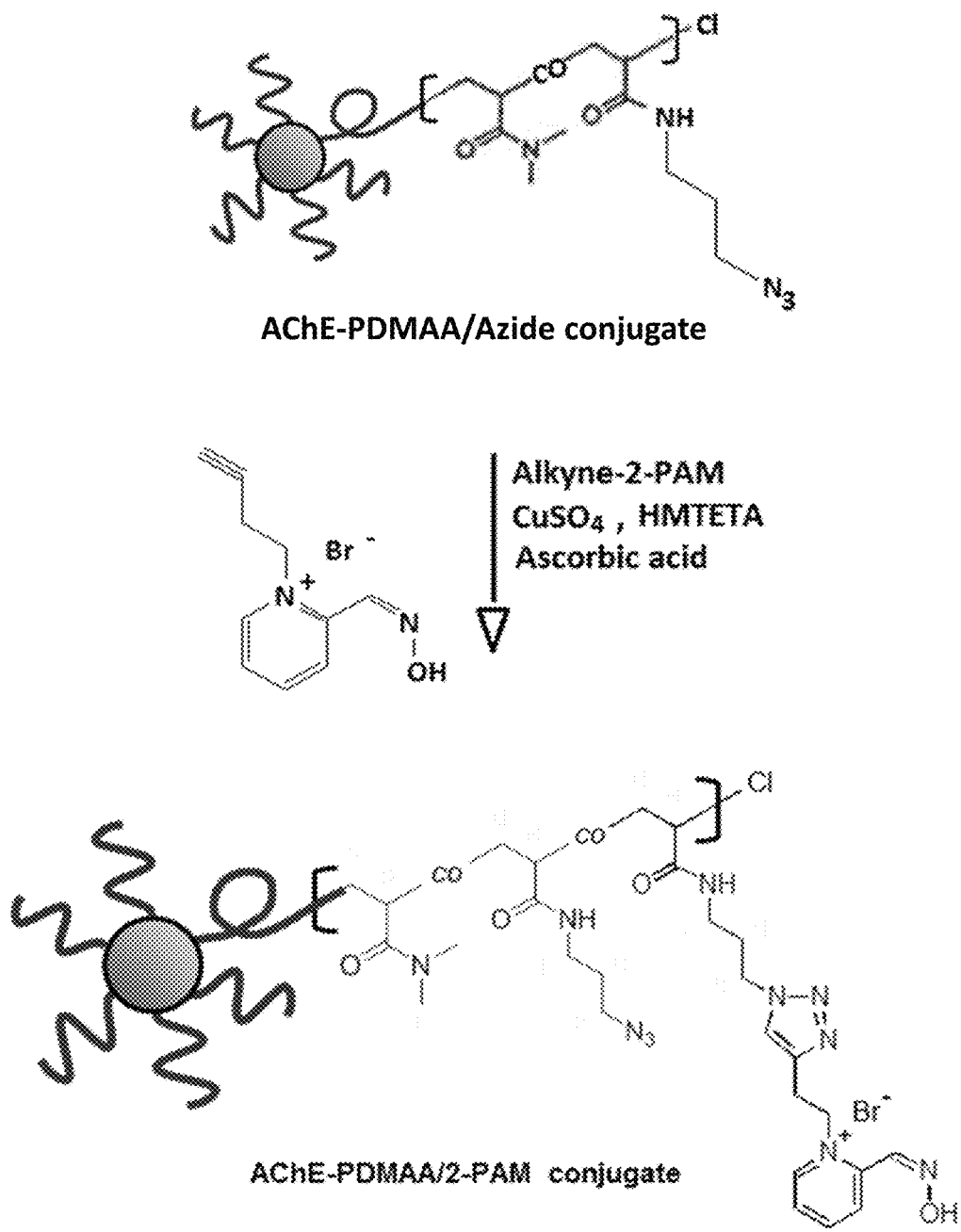
Figure 6D:
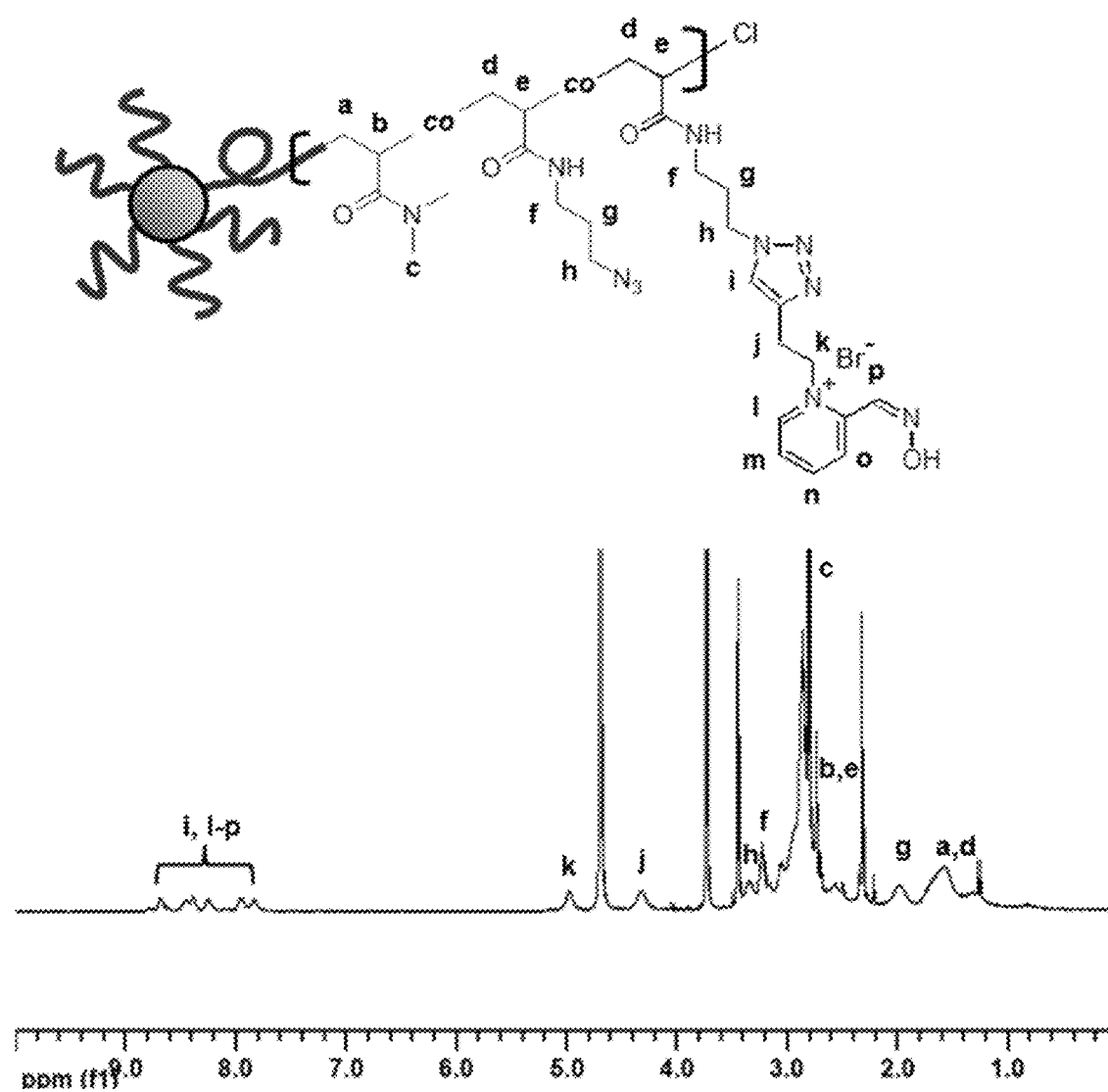

As illustrated in the schematic of FIG. 6C, immobilization of 2-PAM groups to the AChE-PDMAA/Azide conjugate of FIGS. 6A and 6B was carried out by "Click" cycloaddition of alkyne 2-PAM in the presence of a copper catalyst using the following materials and methods: A solution of the AChE-PDMAA/Azide conjugate of FIGS. 6A and 6B (16.2 mg, 33 μmol of azide groups) in 25 mM potassium phosphate buffer (10 mL, pH 7.5) was sealed and bubbled with nitrogen for 50 min. Deoxygenated solution of N-(3-butynyl)-2-pyridinealdoxime (17 mg, 66 μmol), CuSO4 (17 mg, 66 μmol), HMTETA (18 μL, 66 μmop and ascorbic acid (12 mg, 66 μmol) in deionized water (1 mL) was then added to the conjugate solution under nitrogen bubbling. The mixture was sealed and stirred in a refrigerator (4° C.) for 18 h. AChE-PDMAA/2-PAM conjugate was isolated by dialysis with a 50 kDa molecular weight cut off dialysis tube in deionized water in a refrigerator (4° C.) for 24 h and then lyophilized. The chemical structure of obtained AChE-PDMAA/2-PAM conjugate was assigned by NMR spectrum (see FIG. 6D). Molecular weight of AChE-PDMAA/2-PAM conjugate (450.8 kDa) was determined by $^1$H NMR spectrum. $^1$H NMR was used to determine that 50% of the azide groups were bound with alkyne 2-PAM by "Click" cycloaddition. The polymer components of the conjugates were found to have narrow size distribution profiles with lengths governed by the length of the polymerization reaction and monomer content controlled by the relative concentration. It was also found that the reaction could be stopped and resumed with different monomers allowing the generation of well-defined di-block co-polymers. To use ATRP to synthesize the polymers, it may be helpful to change the method of attachment of the oxime groups to the polymer chain. In the synthesis of the AChE-poly-2-PAM, it was found that acrylate derivatives of PAM acted as chain terminators in ATRP and their attachment by quaternization required high temperature, making it less suitable for the enzyme. One chosen way to get around both of these problems is to use ATRP with acrylate monomers with terminal azides and oximes that are synthesized with an alkyne and then added to the polymer through "Click chemistry" (see Table 1).

The terms "Click chemistry," "Click cycloaddition," "Clickable," and "Click reactions" refer to chemical reactions that are high yielding, wide in scope, create only by products that can be removed without chromatography, are stereospecific, simple to perform, and can be conducted in easily removable or benign solvents. Vyas, S., Hadad CM, Reactivation of model cholinesterases by oximes and intermediate phosphyloximes: A computational study, *Chem Biol Interact*, 175(1-3): 187-191 (2008), which is incorporated in its entirety by reference. Several types of reactions have been identified that fulfill these criteria, thermodynamically-favored reactions that lead specifically to one product such as nucleophilic ring opening reactions of epoxides and aziridines, non-aldol type carbonyl reactions, such as the formation of hydrazones and heterocycles, additions to carbon-carbon multiple bonds, such as oxidative formation of epoxides and Michael Additions, and cycloaddition reactions. Because of the versatility and selectivity of the "Click" reaction a variety of protein polymer conjugates can be designed. These include: polymers with different oxime groups; block copolymers with oxime and environmentally responsive blocks; random co-polymers of chain extender and oxime monomers; polymers with oxime monomers with different length tethers to the polymer backbone; and mixtures of homopolymers. Synthesis of the enzyme-polyoxime conjugates are based on AChE with the inclusion of BChE or other esterase, cholinesterase, or combinations thereof, as an optimization alternative. Alkyne-2-PAM derivatives for "Click" cycloaddition to azide groups on the AChE-polymer conjugate can be prepared by varied synthetic pathways using quaternization, esterification or condensation reaction of 2-pyridinecarboxyaldehyde and alkyne derivatives as shown in Table 1.

TABLE 1

Preparation of "Click" PAM monomers

| Reactant | Synthesis | Product |
|---|---|---|
| syn-2-pyridinealdoxime | 4-bromo-1-butyne, acetonitrile, reflux | (N-but-3-ynyl pyridinium bromide with 2-aldoxime) |
| 5-ethynyl-2-pyridinecarboxaldehyde | 1) hydroxylamine, reflux 2) iodomethane, reflux | (4-ethynyl-1-methyl pyridinium iodide with 2-aldoxime) |
| (5-(prop-2-ynyloxy)-2-pyridinecarboxaldehyde) | 1) hydroxylamine, reflux 2) iodomethane, reflux | (5-(prop-2-ynyloxy)-1-methyl pyridinium iodide with 2-aldoxime) |

TABLE 1-continued
Preparation of "Click" PAM monomers
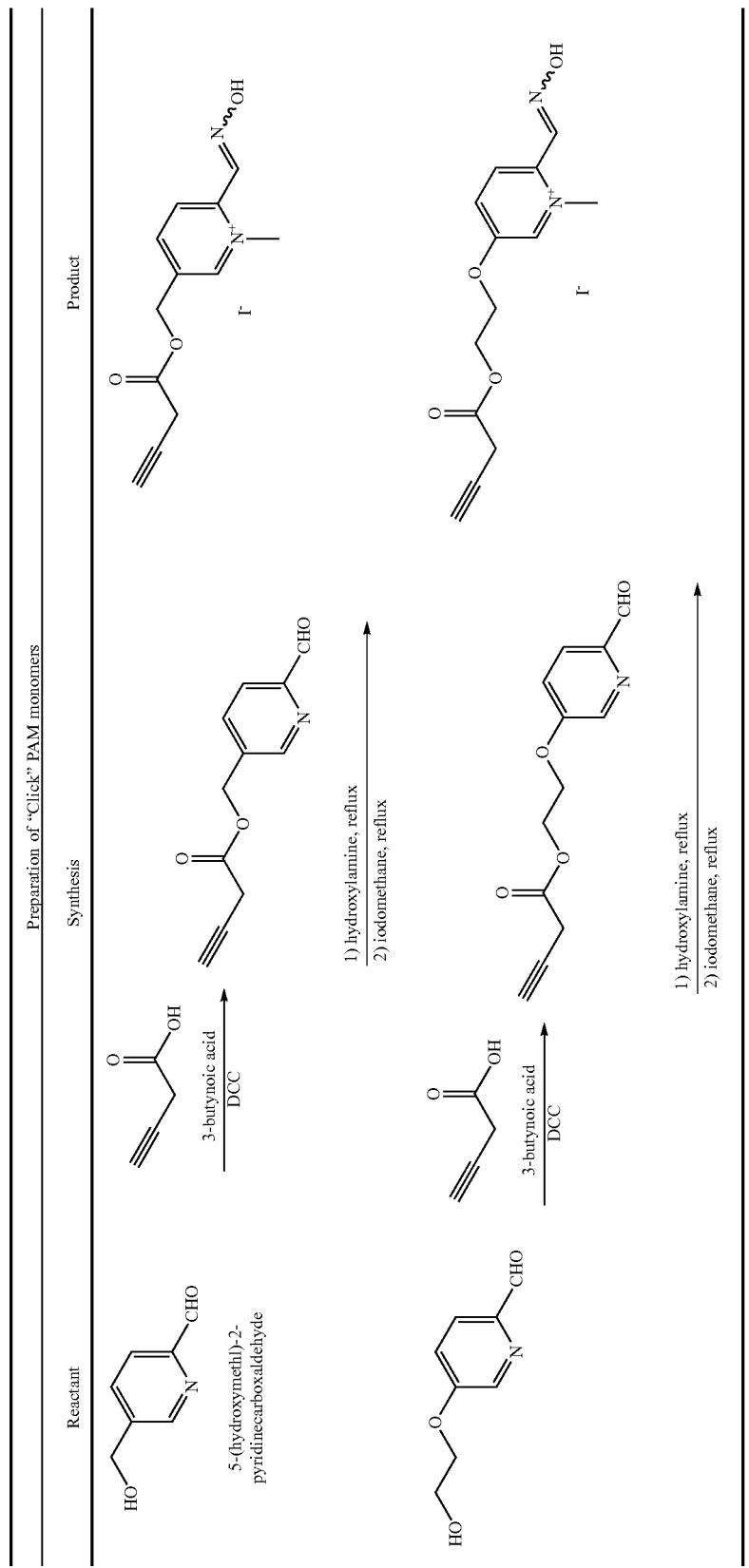

Figure 6E:
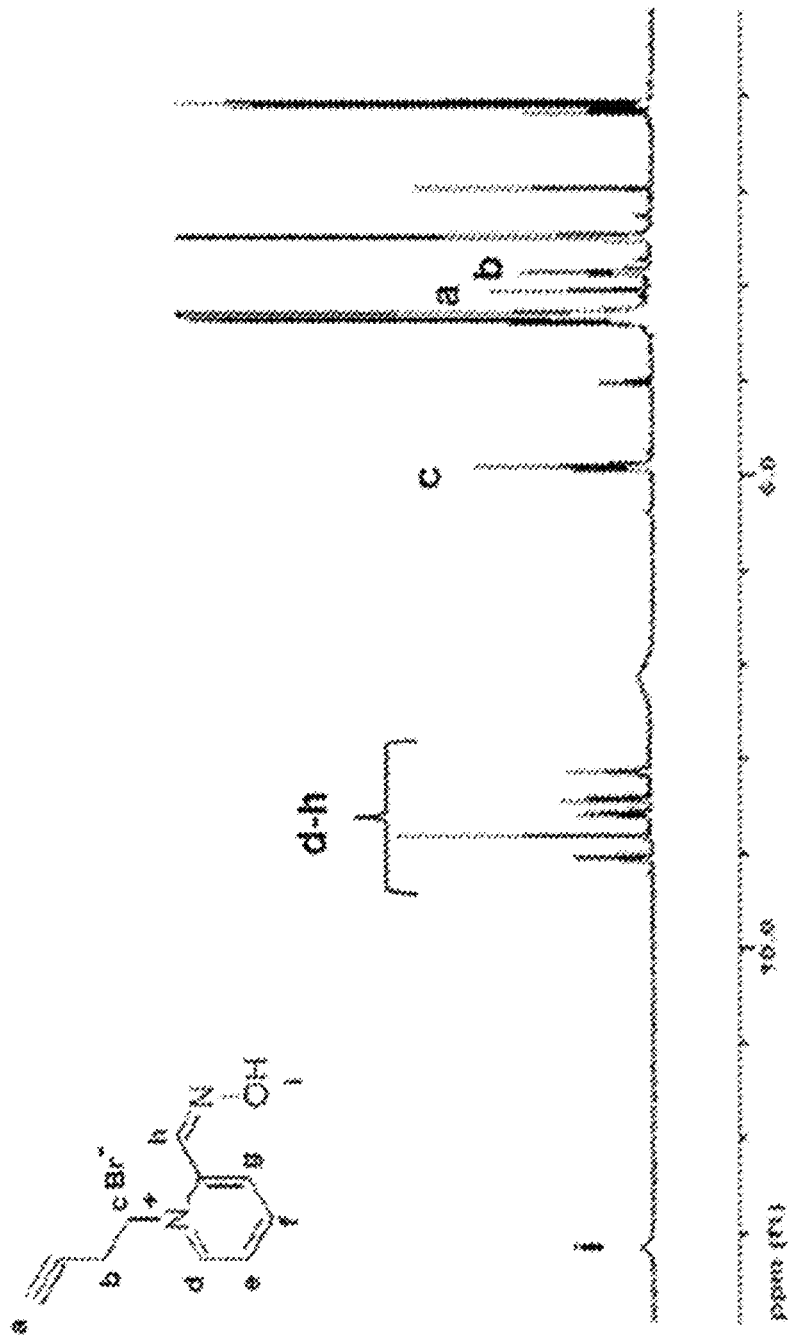

As shown in Table 1, N-(3-butynyl)-2-pyridine aldoxime was synthesized by quaternization of syn-2-pyridinealdoxime and 4-bromo-1-butyne. Synthesis of N-(3-butynyl)-2-pyridine aldoxime includes the following materials and methods: 4-bromo-1-butyne (1.3 g, 10 mmol) was added to a solution of syn-2-pyridinealdoxime (1.0 g, 8.0 mmol) in acetonitrile (100 mL) and refluxed at 100° C. overnight. After cooling down the solution to room temperature, the product was precipitated into diethyl ether. The obtained compound was dried in vacuo: yield 250 mg, $^1$H NMR (spectra shown in FIG. 6E) (300 MHz, DMSO-d6) δ 2.87 (t, 2H, J=6.6 Hz, NCH$_2$CH$_2$C≡CH), 3.07 (s, 1H, NCH$_2$CH$_2$C≡CH), 4.93 (t, 2H, J=6.6 Hz, NCH$_2$CH$_2$C≡CH), 8.14, 8.43, 8.57 and 9.05 (4H, pyridine ring), 8.83 (s, 1H, —CH=NOH), and 13.17 (broad s, 1H, —CH=NOH) ppm.

In a series of optimization rounds of the AChE-poly-2-PAM conjugate, the first round of the optimization process may use derivatives of 2-PAM bound covalently to the polymer backbone by spacers of various chain lengths. Synthesis of other alkyne derivatives of 2-PAM exhibiting varying linkages and alkyl groups (see Table 1) may be achieved using materials and methods known to persons of ordinary skill in the art. In various aspects, other suitable alkyne derivatives of 2-PAM for "Click" cycloaddition to azide groups on the AChE-polymer conjugate are shown in Table 2.

TABLE 2
Alkyne derivatives of 2-pyridine aldoxime
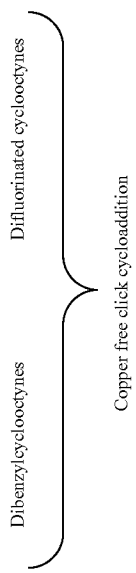

TABLE 2-continued
Alkyne derivatives of 2-pyridine aldoxime
| Structure | Substituents |
|---|---|
|  | $R_2$: —$(CH_2)_nH$, —$(CH_2)_nOH$, —$(CH_2)_nCOOH$, or —$(CH_2)_nNH_2 \cdot HX$<br><br>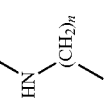 1-alkynes<br><br>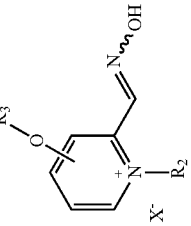 Dibenzylcyclooctynes / Difluorinated cyclooctynes } Copper free click cycloaddition |

TABLE 2-continued
Alkyne derivatives of 2-pyridine aldoxime
| Structure | Substituents |
|---|---|
|  | $R_4$: —$(CH_2)_n$H, —$(CH_2)_n$OH, —$(CH_2)_n$COOH, or —$(CH_2)_n$NH$_2$·HX <br><br> $R_5$: 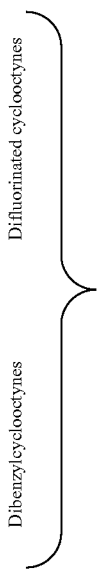 1-alkynes <br><br> Dibenzylcyclooctynes } Copper free click cycloaddition <br> Difluorinated cyclooctynes |

TABLE 2-continued
Alkyne derivatives of 2-pyridine aldoxime
| Structure | Substituents |
|---|---|
| 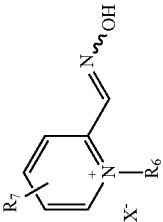 | $R_6$: —(CH$_2$)$_n$H, —(CH$_2$)$_n$OH, —(CH$_2$)$_n$COOH, or —(CH$_2$)$_n$NH$_2$·HX<br><br>$R_7$: 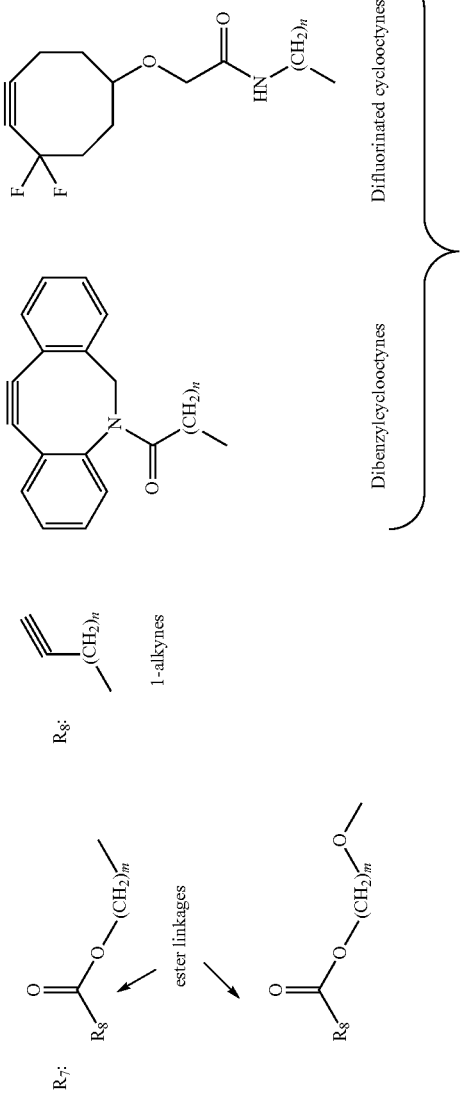 ester linkages → <br><br>$R_8$: 1-alkynes; Dibenzylcyclooctynes, Difluorinated cyclooctynes (Copper free click cycloaddition) |

In various aspects, other rounds of optimization of the AChE-poly-2-PAM conjugate may use derivatives of bis-pyridinium oximes. For example, trimedoxime bromide (TMB-4) or 1,1-methylenebis[4-[(hydroxyimino)methyl]-pyridinium] dimethanesulfonate (MMB-4), and the ketoximes may be used to optimize the structure of the esterase polymer conjugate. (Radie Z et al., Refinement of Structural Leads for Centrally Acting Oxime Reactivators of Phosphylated Cholinesterases, *J. Biol. Chem.*, 287: 11798-11809 (2012). It is pertinent to note that ketoxime analogues of 2-PAM aldoxime generate oximes after their nucleophilic attack on the phosphoryl-ChE conjugates during reactivation of the enzyme. Thus, polymers containing quaternary pyridinium ketoximes (e.g., phenyl or methyl 2-Pyridinium aldoxime methochloride) were also tested as reactivators that could enhance the ability of the polymer-engineered ChE into a true pseudo-catalytic OP hydrolase. Kitz, R J, Ginsburg S, Wilson I B, Activity-structure relationships in reactivation of diethylphosphoryl acetylcholinesterase by phenyl-I-methyl pyridinium ketoximes, *Biochem. Pharmacol*, 14, 1471-1477 (1965); Kuca K, Picha J, Cabal J, Liska F, Synthesis of the three monopyridinium oximes and evaluation of their potency to regenerate acetylcholinesterase inhibited by nerve agents, *I App. Biomed*, 2: 51-56 (2004); Van Hooidonk, C, Krauu G W, and Ginjaar, On the reactivity of organophosphorus compounds Part IV, The alkaline hydrolysis of some 0-phosphylated 2-pyridine oximes, *Rec. Tray. Chim.*, 87, 673-686 (1968). Most enzymes lose activity with multiple turnovers. It is now possible to get multiple turnovers of AChE by incorporating polymeric oximes into the structure of the enzyme.

Figure 7A:
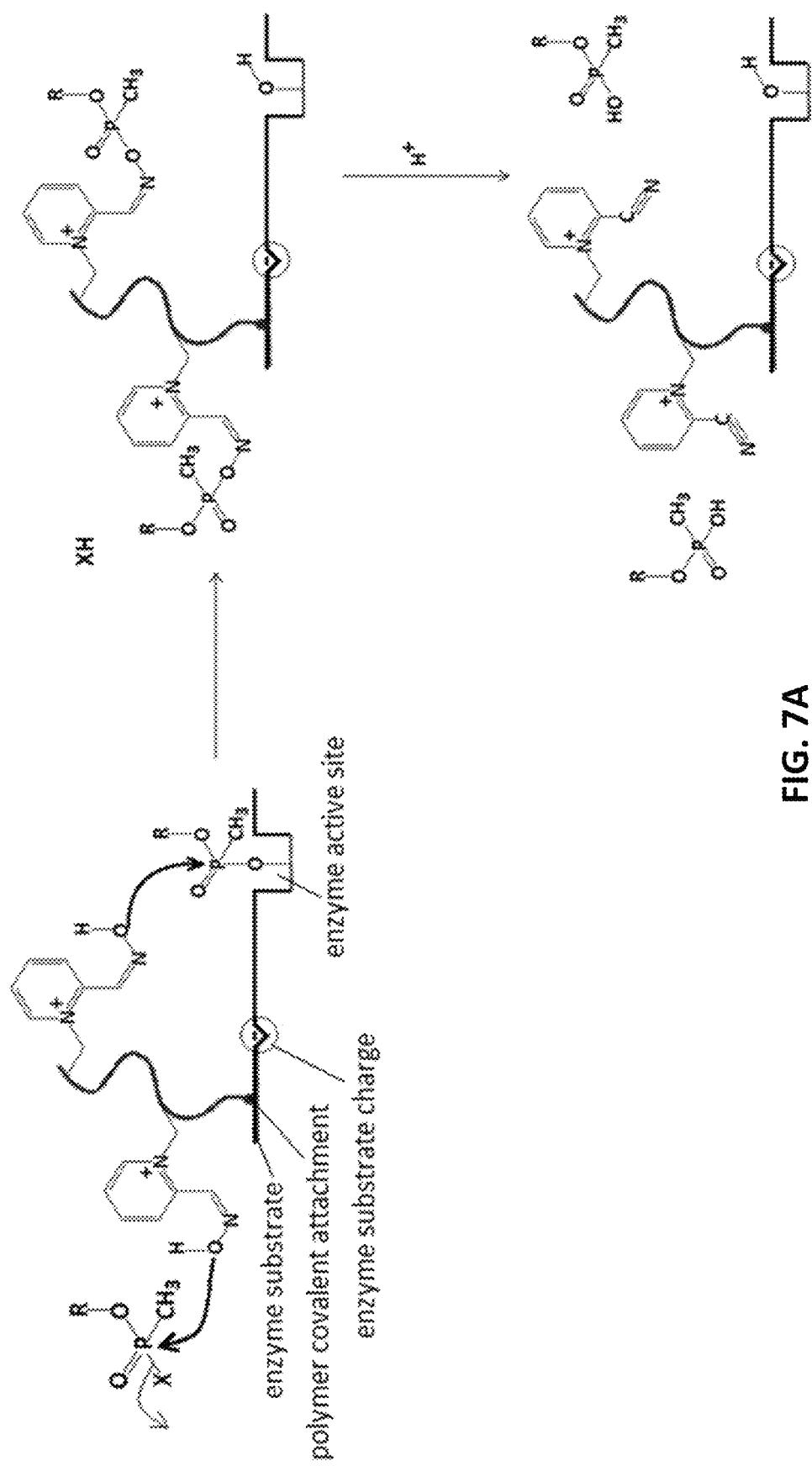
Figure 7B:
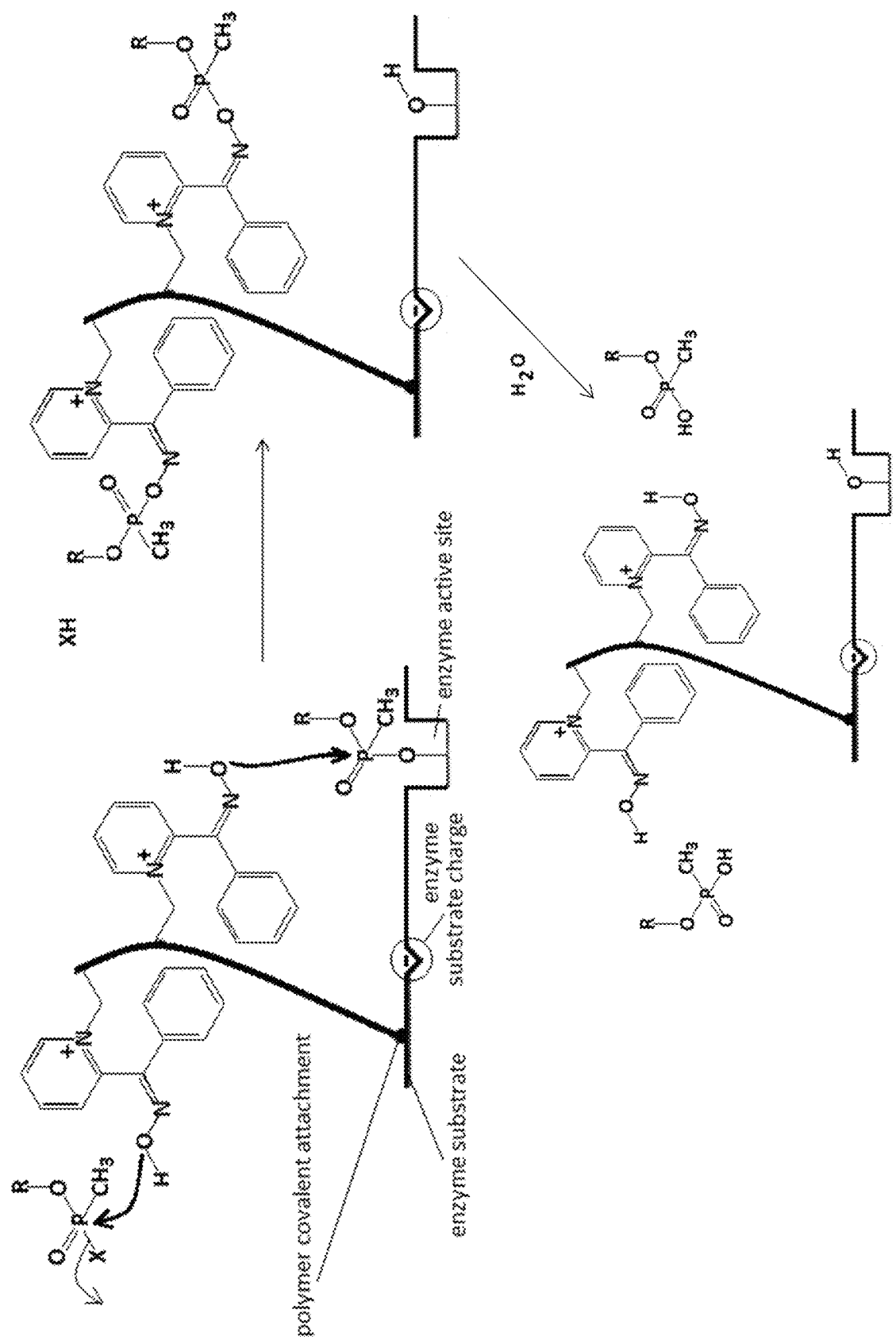

FIGS. 7A and 7B are a schematic diagrams contrasting the predicted reactivation pathways for enzyme polymer attached aldoximes and ketoximes, respectively. The materials and methods for the chemical reactions represented in FIGS. 7A and 7B are discussed in the recent work by Vyas, S., *Chem. Biol. Interact.*, (2008) (supra). The mechanisms shown in FIGS. 7A and 7B provide insight into the interactions of aldoximes and ketoximes with OP compounds. As shown in FIG. 7B, the AChE-ketoxime polymer conjugate is schematically shown to remove the phosphoryl molecule from the AChE active site. The removal of the inhibitor thus regenerates the AChE and subsequently reacts the ketoxime/phosphoryl polymer with water to self-regenerate the ketoxime molecule. The mechanism as shown in FIGS. 7A and B demonstrates that the strong nucleophilic attack of the oxime functional group provided by the esterase polymer conjugate can remove the phosphoryl functional group from the enzyme active site with relative ease resulting in the regenerated enzyme. The facility of the oxime functional group to regenerate the enzyme from the inhibited state is directly due to the proximal availability of the nucleophilic oxime to the active site. This is especially advantageous since the esterase delays clearance of the oxime antitoxin from the body and provides for the oxime antitoxin molecule to remain, not only in the body but at the active site ready to detoxify and regenerate the enzyme upon inhibition. Similarly, regeneration of any enzyme active site inhibited by a phosphoryl functional group would be a candidate for enzyme polyoxime conjugate regeneration. Furthermore, the delayed clearance of the oxime functional group due to its covalent attachment to the enzyme provides prolonged availability for the oxime antitoxin to detoxify not only OP toxins within the active site, but also those OP molecules free in the bodily fluid.

The fact that there is an alkyl or aryl instead of a proton on the carbon atom bound via a double bond to the —NOH moiety is a chemical basis for preventing the oxime from being converted to nitrile with it remaining an oxime (ketoxime in this case) after hydrolysis of the phosphoryl-ketoxime intermediate. The alkyl or aryl may prevent the Beckman rearrangement aided by the proton that converts the aldoxime into a nitrile —CN group (as it happens with aldoximes that bear a proton on the respective carbon atom, see FIG. 7A). This reaction is harnessed with ketoxime-phosphoryl conjugates that are also formed during reactivation. Importantly, ketoximes are usually less active than aldoximes except for few cases such as the phenyl ketoxime analogue of 2-PAM as reported Kuca K, Picha J, Cabal J, Liska F, Synthesis of the three monopyridinium oximes and evaluation of their potency to regenerate acetylcholinesterase inhibited by nerve agents, *J. App. Biomed.*, 2: 51-56 (2004). Ketoxime "Click" monomers can be synthesized essentially as shown for the 2-PAM derivatives (see Tables 1 and 2).

In the first round, optimization of the self-reactivation ability of the esterase polymer conjugate is of concern with random co-polymers and block copolymers of oximes and either spacer monomers (for example, DMAA) and/or environmentally responsive monomers as the variables. In various aspects, the number of monomers within a polyoxime may range from about 1 to about 10 monomers, from about 1 to about 25 monomers, from about 10 to about 50 monomers, from about 1 to about 100 monomers, from about 25 to about 500 monomers, from about 500 to about 1 million monomers, or more than about 1 monomer, more than about 10 monomers, more than about 100 monomers, more than about 1000 monomers, or more than about 1 million monomers. As used herein the term "environmentally responsive" refers to monomers that respond to environmental conditions such as pH, temperature, pressure, chemical concentrations, a change in light energy, a change in electrical charge, or the like, and combinations thereof. For example, a non-exhaustive list of suitable environmentally responsive monomers and their responding conditions is given in Table 3 shown below:

TABLE 3

Environmentally responsive monomers and their responding conditions

| | |
|---|---|
| (structure) | Poly(N-isopropylacrylamide)<br>Thermo-responsive polymer<br>Lower critical solution temperature (LCST) ~33° C. |

TABLE 3-continued

Environmentally responsive monomers and their responding conditions

Poly(oligo(ethylene glycol) methyl ether methacrylate)
Thermo-responsive polymer
Lower critical solution temperature (LCST): 35-82° C.

Poly(sulfobetaine methacrylate)
Thermo-responsive polymer
Upper critical solution temperature (UCST): 10-60° C.

Poly(N,N-dimethylaminoethyl methacrylate)
Thermo- and pH responsive polymer
Lower critical solution temperature (LCST): 38° C.
pH critical point: ~9.0

Poly((methy)acrylate)
pH responsive polymer
pH critical point: ~2.0

Poly(N-acryloyl-6-aminohexanoic acid))
pH responsive polymer
pH critical point: ~4.5

It has been shown that polyDMAEMA conjugated to chymotrypsin predictably affects the local pH of the complex. Murata H, Cummings C S, Koepsel R R, Russell A J, Polymer-Based Protein Engineering Can Rationally Tune Enzyme Activity, pH-Dependence, and Stability, *Biomacromolecules,* 10:14(6):1919-26 (2013).

Incorporating DMAEMA or other pH responsive monomers into the oxime polymer can raise (or lower) the local pH to match the pKa of the oxime groups (e.g., 7.8-8.1 for 2-PAM compounds) and increase their activity in physiological conditions. Thus, inclusion of pH responsive monomers will be a point of emphasis for a second round of esterase polymer conjugate optimization. Additionally, the spacing between the oxime functionality and the polymer backbone could affect access of the oxime to the active site and will be another optimization target with spacers being alkyl chains or short oligomers (e.g., PEG chains of 3-10 monomers). Optimization utilizing spacers of alkyl chains or short oligomers may include alkyl chains from about 1 carbon to about 100 carbons, from about 2 carbons to about 75 carbons, from about 10 carbons to about 50 carbons, from about 4 carbons to about 10 carbons, or for any range subsumed therein, for example, from about 3 carbons to about 20 carbons. Further optimizations could include, enzyme conjugates with multiple different polymers, polymers of multiple oximes, and variations in the number of polymer per protein molecule. Other suitable polymers for optimization of the esterase polymer conjugate may include non-oxime monomers as shown in Table 4 below:

TABLE 4

| Non-oxime Monomers | |
|---|---|
| [structure] | N,N-dimethacrylamide |
| [structure] | N-isopropylacrylamide<br>thermo-responsive |
| [structure] | Carboxyl acrylamide<br>pH-responsive<br>muco-adhesive |
| [structure] | N,N-dimethyaminoethyl methacrylate<br>thermo and pH-responsive<br>muco-adhesive |
| [structure] | (meth)acrylate<br>R: H or $CH_3$<br>pH-responsive<br>muco-adhesive |

TABLE 4-continued

| Non-oxime Monomers | |
|---|---|
| [structure] | 2-hydroxylethyl methacrylate<br>biocompatible |
| [structure] | oligo(ethylene glycol) methyl ether methacrylate<br>thermo-responsive |
| [structure] | N-(2-Hydroxypropyl) methacrylamide<br>biocompatible |
| [structure] | Quaternary ammonium monomer<br>muco-adhesive |
| [structure] | Sulfobetain methacrylate<br>thermo-responsive |

For example, suitable non-oxime and oxime monomers may include aldoximes, ketoximes, muco-adhesion monomers, polyethylene glycol, bis-pyridinium oximes, N,N-dimethylacrylamide, N-isopropylacrylamide, (meth)acrylate, N,N-dimethylaminoethyl methacrylate, carboxyl acrylamide, 2-hydroxylethylmethacrylate, N-(2-hydroxypropyl)methacrylamide, quaternary ammonium monomers, sulfobetain methacrylate, oligo(ethylene glycol) methyl ether methacrylate, 2-PAM monomers, 4-PAM monomers, "Clickable" azide monomers, and combinations thereof. It should be noted that most of these modifications could be performed by many suitable known polymerization methods, such as controlled radical polymerization or on a common base azide containing polymer using "Click" reactions with a variety of monomers. For example, "Click" reactions may be used with 2-PAM monomers, 4-PAM monomers, "Clickable" azide monomers, and derivatives thereof as shown below in Table 5.

TABLE 5

Oxime and Clickable monomers

2-PAM monomer
$R_1$: H or $CH_3$
$R_2$: O or NH

4-PAM monomer
$R_1$: H or $CH_3$
$R_2$: O or NH

"Clickable" azide monomer
$R_1$: H or $CH_3$
$R_2$: O or NH
Click cycloaddition with alkyne 2-PAM Example 4

In a recent investigation of the modification of AChE with a poly[3-(N-2-methacryloyloxyethyl-N,N-dimethyl)ammonatopropanesulfonate] (PMAPS) polymer, an enzyme activity assay determined a 1.6 fold enzyme activity over the unmodified enzyme. It is believed that the differential in enzyme activity is due to the negative charges on the polymer attracting the enzyme substrate through charge-charge interactions leading to a lower KM for the substrate (see FIG. 8). The poly(quaternary ammonium) (PQA) conjugate lost activity because the positive charges repelled the substrate. Additionally, the quaternary amine moieties on the polymer may block access to the active site thus acting as a competitive inhibitor.

Figure 8:
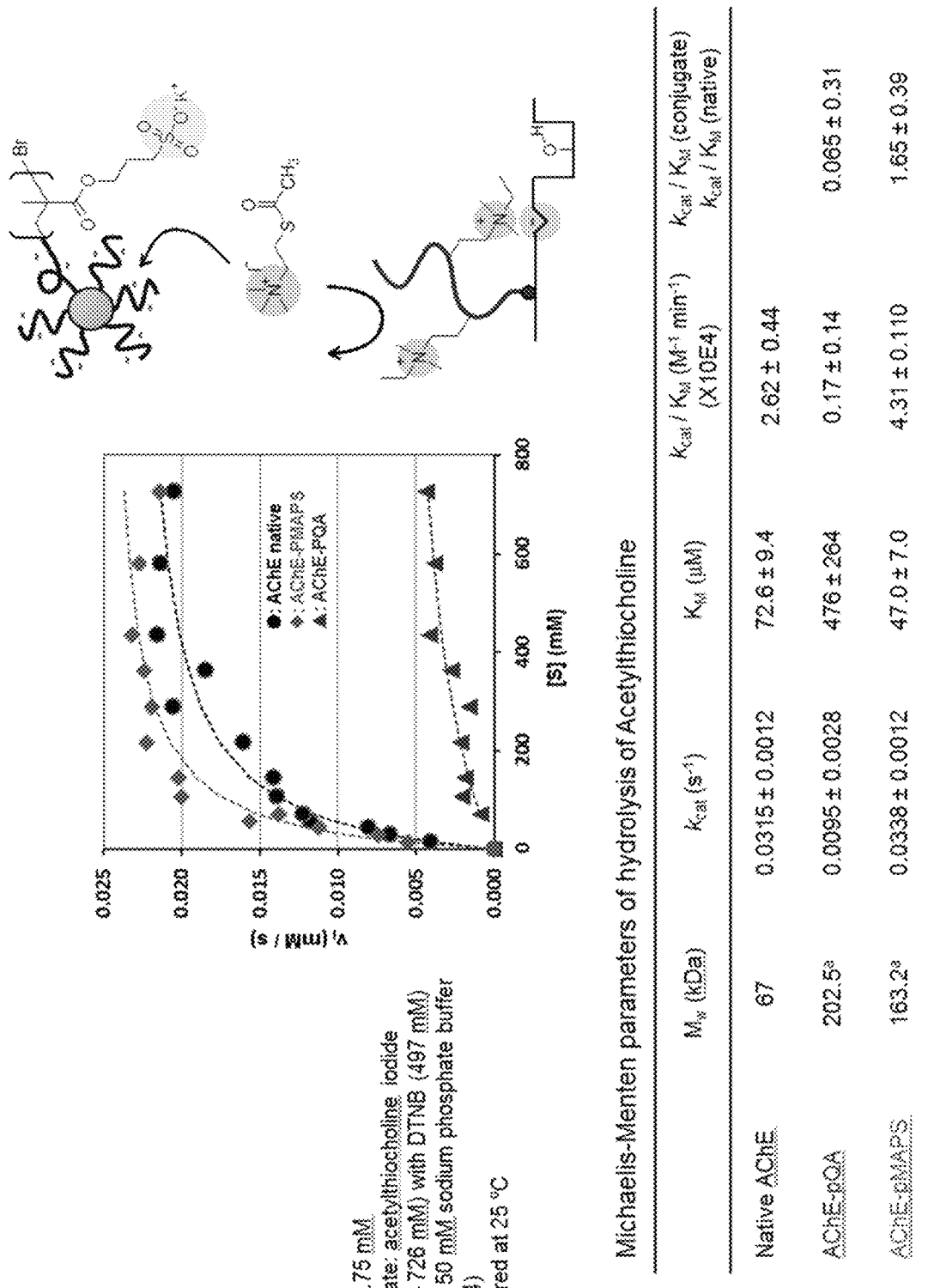

AChE-pMAPS and AChE-pQA as shown in FIG. 8 were synthesized by "grafting-from" ATRP from an AChE-initiator conjugate using MAPS ([3-(N-2-methacryloyloxyethyl-N,N-dimethyl)ammonatopropanesulfonate]) and Quaternary ammonium (QA) monomer (2-(dimethylethylammonium)ethyl methacrylate), respectively. Details of the synthetic method are disclosed in Example 2 herein. The enzyme activity of the AChE-pMAPS and AChE-pQA conjugates was determined using the following materials and methods: Acetylthiocholine iodide (14.5 mM to 726 mM) and DTNB (497 mM) was added to sodium phosphate buffer (990 μL to 940 μL of 50 mM, pH 7.4). Native AChE or conjugates solution (0.75 mM) was added to the substrate solution. The initial rate of hydrolysis of the acetylcholine iodide was monitored by recording the increase in absorption at 412 nm using a UVNIS spectrometer. The Michaelis-Menten kinetic constants for the reaction (kcat, KM, and kcat/KM) were determined by nonlinear curve fitting of plots of initial rate versus substrate concentration using the Enzfitter software.

Future Studies for Polymer-Enzyme Conjugate Molecular Analysis

Similar to the analysis of the esterase polymer conjugates described herein, ongoing research not currently complete will include the following studies. Engineered proteins will be analyzed for polymer conformation and size by gel permeation chromatography (GPC), dynamic light scattering, and NMR. Conjugates will be tested in solution for enzymatic activity by measuring kinetic values and activity maxima for temperature and pH. The susceptibility to inhibition by paraoxon and DFP (as surrogates for the OP toxins) as well as reactivation kinetics and enzyme stability will also be measured. Soluble forms of the conjugated polymers will be tested with native enzyme in parallel with the polymer-protein conjugates to determine the influence of the polymer separately from the conjugation. The influence of the various conjugated polymers will be determined by the performance of the polymer-AChE conjugate compared to native enzyme in solution.

The following enzyme assays will be performed as measures of therapeutic efficacy in vitro:

a) Evaluation of rate of direct interaction of oxime monomers, polymer bound oximes and enzyme-polymer-oxime conjugates with paraoxon and diisopropyl fluorophosphate (DFP) sarin and VX in physiological buffer solution pH 7.4, 37° C. Initial activity of native AChE or 2-PAM conjugate may be monitored and then diluted to give a OD/sec of 0.2-0.4. The activity assay buffer may contain 50 mM sodium phosphate pH 7.4, 1 mM acetylthiocholine iodide and 0.74 mM 5, 5'-Dithiobis (2-nitrobenzoic acid). The rate of hydrolysis of the substrate would be monitored for the first 30 s by the increase in absorption at 412 nm in a spectrophotometer at 25° C.

b) In vitro reactivation studies with oxime monomers and polymer-bound oximes toward paraoxon and DFP, sarin and VX inhibition of AChE (AChE activity will be measured by the Ellman method). The Ellman method uses Ellman's reagent (5,5'-dithiobis-(2-nitrobenzoic acid) or DTNB) as a chemical used to quantify the number or concentration of thiol groups in a sample. The method is named for George L. Ellman. Native AChE and the AChE-2-PAM conjugate ($3.6 \times 10^{-7}$ M) were inhibited with Paraoxon ($1 \times 10^{-6}$ M). Aliquots will be sampled out into activity assay buffer containing 50 mM sodium phosphate pH 7.4, 1 mM acetylthiocholine iodide and 0.74 mM 5, 5'-Dithiobis (2-nitrobenzoic acid), and the optical density (OD)/sec will be monitored for a decrease in the OD/sec to achieve 90-95% inhibition. The inhibited enzyme would then be diluted 1:50 in either 0.25 mM 2-PAM solution or into buffer. Aliquots will be sampled out into activity assay buffer and the Δ OD/sec will be monitored for an increase in the OD/min.

The rate of hydrolysis of substrate would be monitored by the increase in absorption, for example, at 412 nm.

c) In vitro inhibition and self-regeneration in AChE and BChE conjugated to Oxime-Polymers in the presence of paraoxon and DFP, sarin and VX with various conjugate concentrations, and pH rate-profiles of reactivation. Experimental conditions and analysis will follow established protocols for determining the kinetics of simultaneous activity-inhibition assays as reported in Estevez J, Vilanova E, Model equations for the kinetics of covalent irreversible enzyme inhibition and spontaneous reactivation: Esterases and organophosphorus compounds, *Critical Reviews in Toxicology*, 39(5): 427-448 (2009).

To complete the inhibition of the enzyme, the native AChE and the AChE-2-PAM conjugate ($3.6 \times 10^{-7}$ M) will be inhibited with Paraoxon ($1 \times 10^{-6}$ M). Aliquots will be sampled out into activity assay buffer mentioned above, and the OD/sec will be monitored for a decrease in the OD/sec to achieve 90-95% inhibition. To enable enzyme reactivation, the native AChE and the 2-PAM conjugate ($3.6 \times 10^{-7}$ M) will be inhibited with Paraoxon ($1 \times 10^{-6}$ M). Aliquots will be sampled out into activity assay buffer mentioned above, monitoring the change in optical density per second (OD/sec) for a decrease in OD/sec to achieve 90-95% inhibition.

Figure 9:
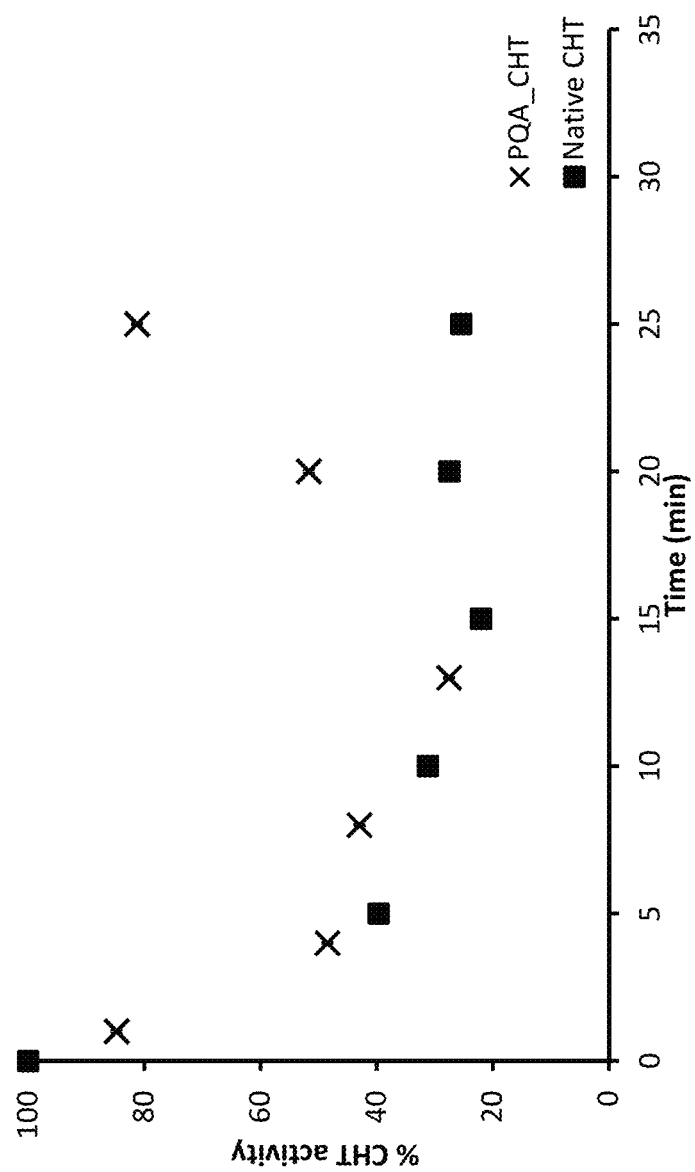

Work has also begun using chymotrypsin (CT) in an enzyme polymer conjugate with poly(quaternary ammonium) (PQA). The PQA-CT conjugate was synthesized by chemically attaching PQA chains to the surface of the CT enzyme. An enzyme inhibition assay was completed using the previously described materials and methods. The results of the preliminary study are shown in FIG. 9. The concentration of the native enzyme was 3.9E-09M and the PQA-CT conjugate was 1.89E-08M in the inhibition reaction. The results of the inhibition assay shows that the PQA-CT conjugate appears to have self-regenerated in the presence of high concentrations of diisopropyl fluorophosphate (DFP).

The work to confirm and expand on the subject of utilizing chymotrypsin-polymer conjugates as regenerating bioscavengers is not complete at the time of the filing of this patent application.

The composition of the present invention may be used for treatment of exposure to organophosphates and is suitable for human and mammalian veterinary use. The treatment may consist of a single dose or a plurality of doses over a period of time. The composition may be administered by any suitable known method, including, without limitation, by oral administration in liquid or tablet form, parenteral administration (The term "parenteral" as used herein refers to modes of administration which include intraarticular injection, intravenous injection, intrarterial injection, subcutaneous intramuscular injection, intrastemal injection, intraperitoneal injection, or infusion, including direct infusion to a target organ or organs), or by intranasal or inhalation techniques, depending on the amount and nature of the exposure and dosage deemed appropriate under the circumstances. For example, the appropriate dosage under circumstances of a single exposure arising, for example, from an accident where the amount of organophosphate can be roughly determined may be calculated with greater accuracy than the dosage needed under circumstances of mass exposure arising, for example, from chemical warfare or a terrorist attack where the amount of exposure may vary for each exposed individual. Mass exposure and the need for rapid response times may require standard dosages that conform to an average body weight for exposed individuals. The dose of the composition will typically also vary depending on the symptoms, age, gender, body weight, and extent of exposure, if known, of the individual patient (human or other mammal). Those skilled in the art can set an appropriate dose and administration schedule if multiple doses are deemed necessary or desirable, taking into consideration the foregoing factors as well as the condition of the patient, the number of patients, and the particular route of administration. The compositions of the present invention designed for pharmaceutical uses will be formulated and dosed in a fashion consistent with good medical practice, taking into account the clinical condition of the individual patient, the site of delivery, the method of administration, the scheduling of administration, and other factors known to practitioners. As stated previously, the required dose of the regenerating esterase polyoxime conjugate according to any of the aspects described herein, is expected to be significantly reduced by, for example, 1-2 orders of magnitude, as compared to stoichiometric free oximes and/or free cholinesterases heretofore reported. The "effective amount" for purposes herein is thus determined by such considerations. In various aspects, the effective amount of the composition administered to a patient suffering from organophosphate toxin exposure is an amount necessary to reduce and preferably eliminate, the inhibition of the normal esterase function. Reduction short of elimination is preferably sufficient to prevent death of the individual due to the esterase inhibition. The dosage amount relative to the body weight of the individual patient and route of administration will be subject to therapeutic discretion.

In various aspects, the composition may be used with a pharmaceutically acceptable salt. As used herein, "pharmaceutically acceptable" means compositions and molecular forms and ingredients of the compositions that are physiologically tolerable and do not produce toxic reactions when administered to a mammal. Pharmaceutically acceptable compositions may be listed in the U.S. or other recognized pharmacopeia for use with mammals and in particular, for use with humans.

Some pharmaceutically acceptable salts are acetate, adipate, aspartate, benzoate, besylate, bicarbonate/carbonate, bisulphate/sulphate, borate, citrate, formate, fumarate, gluconate, glucuronate, hexafluorophosphate, hydrochloride/chloride, hydrobromide/bromide, hydroiodide/iodide, lactate, malate, maleate, malonate, mandelates, mesylate, methylsulphate, naphthylate, 2-napsylate, nicotinate, nitrate, oxalate, palmitate, pamoate, phosphate/hydrogen phosphate/dihydrogen phosphate, pyroglutamate, salicylate, saccharate, stearate, succinate, sulfonate, stannate, tartrate, tosylate, and trifluoroacetate salts. Known basic salts may also be used in certain aspects.

In various aspects, the compositions of the present invention may be administered alone or in combination with a pharmaceutically acceptable carrier or diluent by any of the routes of administration described herein. In various aspects, the compositions of the present invention may be administered alone or in combination with a pharmaceutically acceptable additive or excipient. For example, any one or more of the above mentioned salts may be added to the carrier or diluent, or in certain aspects, may be incorporated in one or more of the monomers of the polymers bound to the esterase. The compositions may be administered in single or multiple doses once or over a period of time. In various aspects, the compositions may be administered as part of a combination therapy with another pharmaceutical agent.

Such carriers may include solid diluents or fillers, sterile aqueous media and various non-toxic organic solvents, etc.

Moreover, oral pharmaceutical compositions can be suitably sweetened and/or flavored. In general, the therapeutically effective compounds of this invention are present in such dosage forms at concentration levels ranging about 1.0% to about 98% by weight, or from about 2% to about 95% by weight, or about 5.0% or 10% to about 90%, 85%, 80%, 75%, 70%, 65%, 60%, or 50% by weight.

For oral administration, tablets containing various excipients such as microcrystalline cellulose, sodium citrate, calcium carbonate, dicalcium phosphate and glycine may be employed along with various disintegrants such as starch, together with granulation binders like polyvinylpyrrolidone, sucrose, gelatin and acacia. Additionally, lubricating agents such as magnesium stearate, sodium lauryl sulfate and talc are preferred for tableting purposes. Solid compositions of a similar type may also be employed as fillers in gelatin capsules; preferred materials in this connection also include lactose or milk sugar as well as high molecular weight polyethylene glycols. When aqueous suspensions are desired for oral administration, the active compositions may be combined with various sweetening or flavoring agents, coloring matter or dyes, and, if so desired, emulsifying and/or suspending agents known to those skilled in the pharmaceutical fields, as well, together with such diluents as water, ethanol, propylene glycol, glycerin and various like combinations thereof.

For parenteral administration, a compound according to any aspect of the present invention may be suspended in solutions or suspensions of a pharmaceutically acceptable oil or aqueous propylene glycol. The aqueous solutions should preferably be compatible with the physiological pH of the individual recipient, for example, greater than a neutral, and preferably greater than pH 8, but less than a deleterious level. The liquid diluents are preferably isotonic. All solutions must be prepared under sterile conditions by standard pharmaceutical techniques well-known to those skilled in the art. Oily solutions are preferred for intra-articular, intra-muscular and subcutaneous injection. Aqueous solutions are preferred for intravenous injection. Typically, the carriers will be water or saline which will be sterile and pyrogen free. The compositions of the present invention, in various aspects, are believed to be well suited to formulation in aqueous carriers such as sterile pyrogen free water, saline or other isotonic solutions. Some or all of the compositions described herein for pharmaceutical applications may be formulated well in advance in aqueous form, for instance, weeks or months or longer time periods before being dispensed.

Formulations suitable for parenteral administration include aqueous and non-aqueous sterile injection solutions which may contain anti-oxidants, buffers, bacteriostats and solutes which render the formulation appropriate for the intended recipient; and aqueous and non-aqueous sterile suspensions which may include suspending agents and thickening agents. The formulations may be presented in unit-dose or multi-dose containers, for example, sealed ampules, vials or syringes, and may be stored in a freeze-dried (lyophilized) condition requiring only the addition of the sterile liquid carrier, for example, water for injections, immediately prior to use. Extemporaneous injection solutions and suspensions may be prepared from sterile powders.

It should be understood that this disclosure is not limited to the various aspects or embodiments disclosed herein, and it is intended to cover modifications that are within the spirit and scope of the invention, as defined by the claims.

What is claimed is:

1. A method comprising administering a bioscavenger to an individual identified as having been exposed to an organophosphate toxin, wherein the bioscavenger comprises at least one polymer covalently conjugated to an esterase, and wherein the at least one polymer comprises a plurality of oxime functional groups.

2. The method of claim 1, wherein, upon exposure of the bioscavenger to an organophosphate toxin, the method further comprises reacting at least one of the plurality of oxime functional groups with at least one covalently inhibited residue of the esterase to detoxify the organophosphate toxin and regenerate the bioscavenger.

3. The method of claim 1, wherein the plurality of oxime functional groups comprises an oxime functional group positioned to exert, in use, a nucleophilic attack on a phosphoryl functional group of an inhibitor when the phosphoryl functional group is attached to an active site of the esterase, and wherein said nucleophilic attack results in removal of the phosphoryl functional group from the active site.

4. The method of claim 1, wherein the esterase comprises chymotrypsin and the plurality of oxime functional groups comprises an aldoxime.

* * * * *

UNITED STATES PATENT AND TRADEMARK OFFICE
CERTIFICATE OF CORRECTION

PATENT NO. : 10,954,506 B2
APPLICATION NO. : 16/556739
DATED : March 23, 2021
INVENTOR(S) : Alan J. Russell et al.

It is certified that error appears in the above-identified patent and that said Letters Patent is hereby corrected as shown below:

On the Title Page

Item (56) Other Publications Column 2, Line 37 delete "activityperspective,"" and insert
-- activity perspective," --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*